US012037395B1

(12) United States Patent
Chen et al.

(10) Patent No.: US 12,037,395 B1
(45) Date of Patent: Jul. 16, 2024

(54) ANTIBODIES BINDING PD-1 AND USES THEREOF

(71) Applicant: IMMVIRA CO., LIMITED, Shenzhen (CN)

(72) Inventors: Mingjiu Chen, Hockessin, DE (US); Wei Tan, San Diego, CA (US)

(73) Assignee: IMMVIRA CO., LIMITED, Shenzhen (CN)

( * ) Notice: Subject to any disclaimer, the term of this patent is extended or adjusted under 35 U.S.C. 154(b) by 939 days.

(21) Appl. No.: 17/047,649

(22) PCT Filed: Apr. 12, 2019

(86) PCT No.: PCT/US2019/027115
§ 371 (c)(1),
(2) Date: Oct. 14, 2020

(87) PCT Pub. No.: WO2019/204132
PCT Pub. Date: Oct. 24, 2019

Related U.S. Application Data

(60) Provisional application No. 62/657,927, filed on Apr. 15, 2018.

(51) Int. Cl.
*A61P 35/00* (2006.01)
*C07K 16/28* (2006.01)

(52) U.S. Cl.
CPC .......... *C07K 16/2818* (2013.01); *A61P 35/00* (2018.01); *C07K 2317/24* (2013.01); *C07K 2317/565* (2013.01); *C07K 2317/74* (2013.01)

(58) Field of Classification Search
CPC ............ C07K 16/2818; C07K 2317/24; C07K 2317/565; A61P 35/00
See application file for complete search history.

(56) References Cited

U.S. PATENT DOCUMENTS

| | | | |
|---|---|---|---|
| 2013/0133091 | A1 | 5/2013 | Korman et al. |
| 2015/0017185 | A1 | 1/2015 | Akbar et al. |
| 2016/0039921 | A1 | 2/2016 | Luo et al. |
| 2018/0011114 | A1 | 1/2018 | Nogami et al. |

FOREIGN PATENT DOCUMENTS

| | | | |
|---|---|---|---|
| RU | 2599417 | C2 | 10/2016 |
| WO | 2006121168 | A1 | 11/2006 |
| WO | 2014179662 | A2 | 11/2014 |
| WO | 2014179664 | A2 | 11/2014 |
| WO | 2015112805 | A1 | 7/2015 |
| WO | 2016014688 | A2 | 1/2016 |
| WO | 2016057841 | A1 | 4/2016 |
| WO | 2016092419 | A1 | 6/2016 |
| WO | 2017058115 | A1 | 4/2017 |
| WO | 2018006005 | A1 | 1/2018 |
| WO | WO-2018053709 | | 3/2018 |

OTHER PUBLICATIONS

Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Kussie et al. A single engineered amino acid substitution changes antibody fine specificity.J Immunol.Jan. 1, 1994;152(1):146-52. (Year: 1994).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding.PNAS Jan. 24, 2017 114(4)E486-E495;f irstpublished Jan. 5, 2017. (Year: 2017).*
International Search Report and Written Opinion for International Application No. PCT/US2019/027115 dated Sep. 10, 2019. (9 pages).

* cited by examiner

*Primary Examiner* — Aurora M Fontainhas
*Assistant Examiner* — Jennifer A Benavides
(74) *Attorney, Agent, or Firm* — Sheppard, Mullin, Richter & Hampton LLP

(57) ABSTRACT

An isolated monoclonal antibody that specifically binds human PD-1. A nucleic acid molecule encoding the antibody, an expression vector, a host cell and a method for expressing the antibody are also provided. The present invention further provides an immunoconjugate, a bispecific molecule, a chimeric antigen receptor, an oncolytic virus and a pharmaceutical composition comprising the antibody, as well as a treatment method using an anti-PD-1 antibody of the invention.

10 Claims, 1 Drawing Sheet

Specification includes a Sequence Listing.

ANTIBODIES BINDING PD-1 AND USES THEREOF

CROSS-REFERENCE TO RELATED APPLICATIONS

This application is a U.S. National Stage Application under 35 U.S.C. § 371 of International Application No. PCT/US2019/027115, filed Apr. 12, 2019, which application claims the benefit of 35 U.S.C. § 119(e) of U.S. Provisional Application No. 62/657,927, filed Apr. 15, 2018, each of which is hereby incorporated by reference in its entirety.

SEQUENCE LISTING

The instant application contains a Sequence Listing which has been filed electronically in ASCII format and is hereby incorporated by reference in its entirety. Said ASCII copy, created on Jun. 21, 2021, is named 320421US_Sequence-Listing.txt and is 81,920 bytes in size.

FIELD OF THE INVENTION

The present invention relates generally to an isolated monoclonal antibody, particularly a mouse, chimeric or humanized monoclonal antibody that specifically binds to human PD-1 with high affinity and functionality. A nucleic acid molecule encoding the antibody, an expression vector, a host cell and a method for expressing the antibody are also provided. The present invention further provides an immunoconjugate, a bispecific molecule, an oncolytic virus, and a pharmaceutical composition comprising the antibody, as well as a diagnostic and treatment method using an anti-PD-1 antibody of the invention.

BACKGROUND OF THE INVENTION

Programmed cell death protein 1, also known as PD-1 or CD279, is a member of the CD28 family of T cell regulators, and expressed on activated B cells, T cells, and myeloid cells (Agata et al., (1996) *Int Immunol* 8:765-72; Okazaki et al., (2002) *Curr. Opin. Immunol.* 14: 391779-82; Bennett et al., (2003) *J Immunol* 170:711-8). It contains a membrane proximal immunoreceptor tyrosine inhibitory motif (ITIM) and a membrane distal tyrosine-based switch motif (ITSM) (Thomas, M. L. (1995) *J Exp Med* 181:1953-6; Vivier, E and Daeron, M (1997) *Immunol Today* 18:286-91). Two ligands for PD-1 have been identified, PD-L1 and PD-L2, both are B7 homologs that bind to PD-1, but do not bind to other CD28 family members.

Several lines of evidence have suggested that PD-1 and its ligands negatively regulate immune responses. For example, PD-1 was found abundant in a variety of human cancers (Dong et al., (2002) *Nat. Med.* 8:787-9). Further, the interaction between PD-1 and PD-L1 was reported to cause a decrease in tumor infiltrating lymphocytes and T-cell receptor mediated proliferation, and immune evasion of cancerous cells (Dong et al., (2003) *J Mol.* Med. 81:281-7; Blank et al., (2005) *Cancer Immunol. Immunother.* 54:307-314; Konishi et al., (2004) *Clin. Cancer Res.* 10:5094-100). Studies also showed that immune suppression can be reversed by inhibiting the local interaction of PD-1 with PD-L1, and the effect was additive when the interaction of PD-1 with PD-L2 was blocked as well (Iwai et al., (2002) *Proc. Nat'l. Acad. Sci. USA* 99:12293-7; Brown et al., (2003) *J Immunol.* 170:1257-66).

PD-1 deficient animals may develop various autoimmune phenotypes, including autoimmune cardiomyopathy and a lupus-like syndrome with arthritis and nephritis (Nishimura et al., (1999) *Immunity* 11:141-51; Nishimura et al., (2001) *Science* 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al., (2003) *J Exp Med* 198:71-78; Prokunina and Alarcon-Riquelme (2004) *Hum Mol Genet* 13:R143; Nielsen et al., (2004) *Lupus* 13:510). In a murine B cell tumor line, the ITSM of PD-1 was shown to be essential to block BCR-mediated $Ca^{2+}$-flux and tyrosine phosphorylation of downstream effector molecules (Okazaki et al., (2001) *PNAS* 98:13866-71).

A number of cancer immunotherapy agents that target PD-1 have been developed for disease treatment. One such anti-PD-1 antibody is Nivolumab (sold under the tradename of OPDIVO® by Bristol Myers Squibb), which produced complete or partial responses in non-small-cell lung cancer, melanoma, and renal-cell cancer, in a clinical trial with a total of 296 patients (Topalian SL et al., (2012) *The New England Journal of Medicine.* 366 (26): 2443-54). It was approved in Japan in 2014 and by US FDA in 2014 to treat metastatic melanoma. Another anti-PD-1 antibody, Pembrolizumab (KEYTRUDA™, MK-3475, Merck) targeting PD-1, was also approved by US FDA in 2014 to treat metastatic melanoma. It is being used in clinical trials in US for lung cancer, lymphoma, and mesothelioma.

Despite the anti-PD-1 antibodies that are already developed and approved, there is a need for additional monoclonal antibodies with enhanced binding affinity to PD-1 and other desirable pharmaceutical characteristics.

SUMMARY OF THE INVENTION

The present invention provides an isolated monoclonal antibody, for example, a mouse, human, chimeric or humanized monoclonal antibody, that binds to PD-1 (e.g., the human PD-1, and monkey PD-1) and has increased affinity to PD-1 and comparable, if not better, anti-tumor effect compared to existing anti-PD-1 antibodies such as Nivolumab.

The antibody of the invention can be used for a variety of applications, including detection of the PD-1 protein, and treatment and prevention of PD-1 associated diseases, such as cancers, autoimmune cardiomyopathy, autoimmune encephalomyelitis, systemic lupus erythematosus, graft-versus-host disease (GVHD), type I diabetes, and rheumatoid arthritis.

Accordingly, in one aspect, the invention pertains to an isolated monoclonal antibody (e.g., a mouse, chimeric or humanized antibody), or an antigen-binding portion thereof, that binds PD-1, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, 99% or 100% identity to (1) SEQ ID NOs: 1, 2 and 3, respectively; (2) SEQ ID NOs: 4, 5 and 6, respectively; (3) SEQ ID NOs: 7, 8 and 9, respectively; (4) SEQ ID NOs: 10, 11 and 12, respectively; (5) SEQ ID NOs: 13, 14 and 15, respectively; (6) SEQ ID NOs: 16, 17 and 18, respectively; (7) SEQ ID NOs: 19, 20 and 21, respectively; (8) SEQ ID NOs: 22, 23 and 24, respectively; (9) SEQ ID NOs: 25, 26 and 27, respectively; (10) SEQ ID NOs: 28, 29 and 30, respectively; or (11) SEQ ID NOs: 31, 32 and 33, respectively, wherein, the antibody, or antigen-binding fragment thereof, binds to PD-1.

In one aspect, an isolated monoclonal antibody, or an antigen-binding portion thereof, of the present invention comprises a heavy chain variable region comprising an amino acid sequence having at least 80%, 85%, 90%, 95%, 98%, 99% or 100% identity to SEQ ID NOs: 67, 68, 69, 70, 71, 72, 73, 74, 75, 76, 77, 78 or 79, wherein the antibody or antigen-binding fragment thereof binds to PD-1. SEQ ID NOs: 67 and 69-79 may be encoded by nucleic acid sequences of SEQ ID NOs: 102-113, respectively.

In one aspect, an isolated monoclonal antibody, or an antigen-binding portion thereof, of the present invention comprises a light chain variable region that comprises a CDR1 region, a CDR2 region and a CDR3 region, wherein the CDR1 region, the CDR2 region, and the CDR3 region comprise amino acid sequences having at least 80%, 85%, 90%, 95%, 98%, 99% or 100% identity to (1) SEQ ID NOs: 34, 35 and 36, respectively; (2) SEQ ID NOs: 37, 38 and 39, respectively; (3) SEQ ID NOs: 40, 41 and 42, respectively; (4) SEQ ID NOs: 43, 44 and 45, respectively; (5) SEQ ID NOs: 46, 47 and 48, respectively; (6) SEQ ID NOs: 49, 50 and 51, respectively; (7) SEQ ID NOs: 52, 53 and 54, respectively; (8) SEQ ID NOs: 55, 56 and 57, respectively; (9) SEQ ID NOs: 58, 59 and 60, respectively; (10) SEQ ID NOs: 61, 62 and 63, respectively; or (11) SEQ ID NOs: 64, 65 and 66, respectively, wherein, the antibody, or antigen-binding fragment thereof, binds to PD-1.

In one aspect, an isolated monoclonal antibody, or an antigen-binding portion thereof, of the present invention comprises a light chain variable region comprising an amino acid sequence having at least 80%, 85%, 90%, 95%, 98%, 99% or 100% identity to SEQ ID NOs: 80, 81, 82, 83, 84, 85, 86, 87, 88, 89, 90, 91, 92, 93, 94, 95 or 96, wherein the antibody or antigen-binding fragment thereof binds to PD-1. SEQ ID NOs: 80 and 86-96 may be encoded by nucleic acid sequences of SEQ ID NOs: 114-125, and, respectively.

In one aspect, an isolated monoclonal antibody, or an antigen-binding portion thereof, of the present invention comprises a heavy chain variable region and a light chain variable region each comprising a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98%, 99% or 100% identity to (1) SEQ ID NOs: 1, 2, 3, 34, 35 and 36, respectively; (2) SEQ ID NOs: 4, 5, 6, 37, 38 and 39, respectively; (3) SEQ ID NOs: 7, 8, 9, 40, 41 and 42, respectively; (4) SEQ ID NOs: 10, 11, 12, 43, 44 and 45, respectively; (5) SEQ ID NOs: 13, 14, 15, 46, 47 and 48, respectively; (6) SEQ ID NOs: 16, 17, 18, 49, 50 and 51, respectively; (7) SEQ ID NOs: 19, 20, 21, 52, 53 and 54, respectively; (8) SEQ ID NOs: 22, 23, 24, 55, 56 and 57, respectively; (9) SEQ ID NOs: 25, 26, 27, 58, 59 and 60, respectively; (10) SEQ ID NOs: 28, 29, 30, 61, 62 and 63, respectively; or (11) SEQ ID NOs: 31, 32, 32, 64, 65 and 66, respectively, wherein the antibody or antigen-binding fragment thereof binds to PD-1.

In one embodiment, an isolated monoclonal antibody, or the antigen-binding portion thereof, of the present invention comprises a heavy chain variable region and a light chain variable region, the heavy chain variable region and the light chain variable region comprising amino acid sequences having at least 80%, 85%, 90%, 95%, 98%, 99% or 100% identity to (1) SEQ ID NOs: 67 and 80, respectively; (2) SEQ ID NOs: 68 and 81, respectively; (3) SEQ ID NOs: 69 and 81, respectively; (4) SEQ ID NOs: 68 and 82, respectively; (5) SEQ ID NOs: 68 and 83, respectively; (6) SEQ ID NOs: 68 and 84, respectively; (7) SEQ ID NOs: 68 and 85, respectively; (8) SEQ ID NOs: 68 and 86, respectively; (9) SEQ ID NOs: 69 and 86, respectively; (10) SEQ ID NOs: 70 and 87 respectively; (11) SEQ ID NOs: 71 and 88, respectively; (12) SEQ ID NOs: 72 and 89, respectively; (13) SEQ ID NOs: 73 and 90, respectively; (14) SEQ ID NOs: 74 and 91, respectively; (15) SEQ ID NOs: 75 and 92, respectively; (16) SEQ ID NOs: 76 and 93, respectively; (17) SEQ ID NOs: 77 and 94, respectively; (18) SEQ ID NOs: 78 and 95, respectively; or (19) SEQ ID NOs: 79 and 96, respectively, wherein the antibody or antigen-binding fragment thereof binds to PD-1.

In one embodiment, an isolated monoclonal antibody, or the antigen-binding portion thereof, of the present invention comprises a heavy chain and a light chain, the heavy chain comprising a heavy chain variable region and a heavy chain constant region, the light chain comprising a light chain variable region and a light chain constant region, wherein, the heavy chain constant region comprises amino acid sequences having at least 80%, 85%, 90%, 95%, 98%, 99% or 100% identity to SEQ ID Nos: 97, 99 or 129, and the light chain constant region comprises amino acid sequences having at least 80%, 85%, 90%, 95%, 98%, 99% or 100% identity to SEQ ID Nos: 98 or 130, and the heavy chain variable region and the light chain variable region comprise amino acid sequences described above, wherein the antibody or antigen-binding fragment thereof binds to PD-1. These amino acid sequences of SEQ ID NOs: 97 and 99 may be encoded by nucleic acid sequences of SEQ ID NOs: 126 and 128, respectively. SEQ ID NO:98 may be encoded by SEQ ID NOs: 127.

The antibody of the present invention in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to PD-1. The antibody of the invention can be a full-length antibody, for example, of an IgG1, IgG2 or IgG4 isotype. The antibody of the present invention in other embodiments may be a single chain antibody, or antibody fragments, such as Fab or Fab'2 fragments.

The antibody, or antigen-binding portion thereof, of the present invention has higher binding affinity to human PD-1 than prior art anti-PD-1 antibodies such as Nivolumab, binding to human PD-1 with a $K_D$ of $6.36\times10^{-9}$M or less and inhibiting the binding of PD-L1 to PD-1. The antibody or antigen-binding portion thereof of the invention also provides comparable, if not better, anti-tumor effect compared to existing anti-PD-1 antibodies such as Nivolumab.

The invention also provides an immunoconjugate comprising an antibody of the invention, or antigen-binding portion thereof, linked to a therapeutic agent, such as a cytotoxin. The invention also provides a bispecific molecule comprising an antibody, or antigen-binding portion thereof, of the invention, linked to a second functional moiety (e.g., a second antibody) having a different binding specificity than said antibody, or antigen-binding portion thereof. In another aspect, the antibody or an antigen binding portions thereof of the present invention can be made into part of a chimeric antigen receptor (CAR). The antibody or an antigen binding portions thereof of the present invention can also be encoded by or used in conjunction with an oncolytic virus.

Compositions comprising an antibody, or antigen-binding portion thereof, or immunoconjugate, bispecific molecule, oncolytic virus, or CAR of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-PD-1 antibody using the host cell comprising the expression vector is also provided, comprising steps of (i) expressing the antibody in the host cell and (ii) isolating the antibody from the host cell or its cell culture.

In yet another aspect, the invention provides a method of modulating an immune response in a subject comprising administering to the subject the antibody, or antigen-binding portion thereof, of the invention such that the immune response in the subject is modulated. Preferably, the antibody of the invention enhances, stimulates or increases the immune response in the subject. In some embodiments, the method comprises administering a composition, a bispecific molecule, an immunoconjugate, a CAR-T cell, or an antibody-encoding or antibody-bearing oncolytic virus of the invention, or alternatively a nucleic acid molecule capable of expressing the same in the subject.

In a further aspect, the invention provides a method of inhibiting tumor growth in a subject, comprising administering to a subject a therapeutically effective amount of the antibody, or antigen-binding portion thereof, of the present invention. The tumor may be a solid or non-solid tumor, including, but not limited to, lymphoma, leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, renal-cell cancer and nasopharynx cancer. In some embodiments, the method comprises administering a composition, a bispecific molecule, an immunoconjugate, a CAR-T cell, or an antibody-encoding or antibody-bearing oncolytic virus of the invention, or alternatively a nucleic acid molecule capable of expressing the same in the subject.

In another aspect, the invention provides a method of treating an infectious disease in a subject, comprising administering to a subject a therapeutically effective amount of the antibody, or antigen-binding portion thereof, of the present invention. In some embodiments, the method comprises administering a composition, a bispecific molecule, an immunoconjugate, a CAR-T cell, or an antibody-encoding or antibody-bearing oncolytic virus of the invention, or alternatively a nucleic acid molecule capable of expressing the same in the subject.

Still further, the invention provides a method of enhancing an immune response to an antigen in a subject, comprising administering to the subject. (i) the antigen; and (ii) the antibody, or antigen-binding portion thereof, such that an immune response to the antigen in the subject is enhanced. The antigen can be, for example, a tumor antigen, a viral antigen, a bacterial antigen or an antigen from a pathogen.

The antibodies of the invention can be used in combination with at least one additional agent such as an immunostimulatory antibody (e.g., an anti-PD-L1 antibody and/or an anti-CTLA-4 antibody), a cytokine (e.g., IL-2 and/or IL-21), or a costimulatory antibody (e.g., an anti-CD137 and/or anti-GITR antibody).

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1:
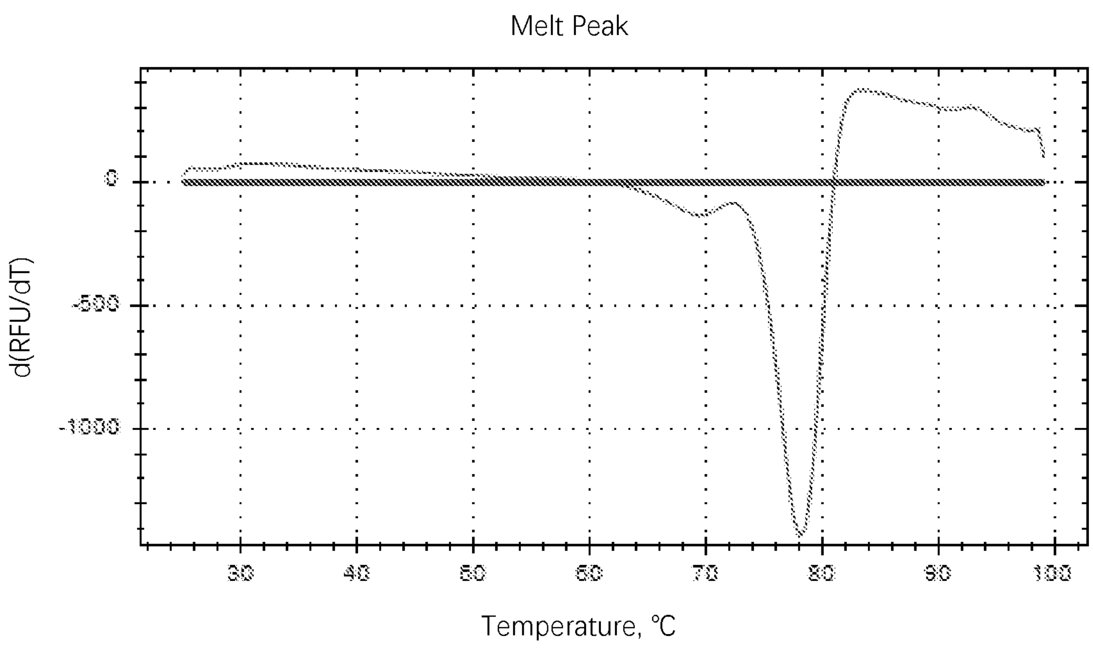
FIG. 1 shows humanized anti-PD-1 antibody huC1E1-V10's melt curve.

To ensure that the present disclosure may be more readily understood, certain terms are first defined. Additional definitions are set forth throughout the detailed description.

The term "PD-1" refers to programmed cell death protein 1. The term "PD-1" comprises variants, isoforms, homologs, orthologs and paralogs. For example, an antibody specific for a human PD-1 protein may, in certain cases, cross-react with a PD-1 protein from a species other than human, such as monkey. In other embodiments, an antibody specific for a human PD-1 protein may be completely specific for the human PD-1 protein and exhibit no cross-reactivity to other species or of other types; or may cross-react with PD-1 from certain other species but not all other species.

The term "human PD-1" refers to an PD-1 protein having an amino acid sequence from a human, such as the amino acid sequence of human PD-1 having Genbank Accession No. NP_005009.2. The terms "monkey or rhesus PD-1" and "mouse PD-1" refer to monkey and mouse PD-1 sequences, respectively, e.g. those with the amino acid sequences having Genbank Accession Nos. NP_001107830 and CAA48113, respectively.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a PD-1 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a PD-1 protein is substantially free of antibodies that specifically bind antigens other than PD-1 proteins). An isolated antibody that specifically binds a human PD-1 protein may, however, have cross-reactivity to other antigens, such as PD-1 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimetic antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human PD-1" is intended to refer to an antibody that binds to human PD-1 protein (and possibly a PD-1 protein from one or more non-human species) but does not substantially bind to non-PD-1 proteins. Preferably, the antibody binds to human PD-1 protein with "high affinity", namely with a $K_D$ of $5.0\times10^{-8}$ M or less, more preferably $1.0\times10^{-8}$ M or less, and more preferably $7.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, even more preferably $7.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$IC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present invention sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the invention are described in further detail in the following subsections.

Anti-PD-1 Antibodies Having Increased Binding Affinity to Human PD-1 and Better Anti-Tumor Effect The antibody, or the antigen-binding portion thereof, of the invention specifically binds to human PD-1 and have improved binding affinity as well as comparable, if not better, anti-tumor effect compared to previously described anti-PD-1 antibodies, particularly compared to Nivolumab.

The antibody, or the antigen-binding portion thereof, of the invention preferably binds to human PD-1 protein with a $K_D$ of $7.0\times10^{-9}$ M or less, more preferably with a $K_D$ of $5.0\times10^{-10}$ M or less. The antibodies of the invention also bind to Cynomolgus monkey PD-1 with a $K_D$ at about $1.0\times10^{-7}$ M to $1.0\times10^{-10}$ M.

Additional functional properties include the capacity to block PD-1/PD-L1 interaction. The antibodies of the present invention, in one embodiment, can inhibit binding of PD-1 to PD-L1 at a similar concentration as Nivolumab.

Other functional properties include the ability of the antibody to stimulate an immune response, such as an antigen-specific T cell response. This can be tested, for example, by assessing the ability of the antibody to stimulate interleukin-2 (IL-2) production in an antigen-specific T cell response. In certain embodiments, the antibody binds to human PD-1 and stimulates an antigen-specific T cell response. In other embodiments, the antibody binds to human PD-1 but does not stimulate an antigen-specific T cell response. Other means for evaluating the capacity of the antibody to stimulate an immune response include testing its ability to inhibit tumor growth, such as in an in vivo tumor graft model or the ability to stimulate an autoimmune response, such as the ability to promote the development of an autoimmune disease in an autoimmune model, e.g., the ability to promote the development of diabetes in the NOD mouse model.

Preferred antibodies of the invention are human monoclonal antibodies. Additionally or alternatively, the antibodies can be, for example, chimeric or humanized monoclonal antibodies.

Monoclonal Anti-PD-1 Antibody

The preferred antibody of the invention is the monoclonal antibody structurally and chemically characterized as described below and in the following Examples. The $V_H$ amino acid sequence of the anti-PD-1 antibody is set forth in SEQ ID NOs: 67, 68, 69, 70, 71, 72, 73, 74, 75, 76, 77, 78 or 79. The $V_L$ amino acid sequence of the anti-PD-1 antibody is shown in SEQ ID NOs: 80, 81, 82, 83, 84, 85, 86, 87, 88, 89, 90, 91, 92, 93, 94, 95 or 96. The amino acid sequence ID numbers of the heavy/light chain variable regions of the antibodies are summarized in Table 1 below, some clones sharing the same $V_H$ or $V_L$. The heavy chain constant region for all clones may be IgG1 heavy chain constant region, such as human IgG1 heavy chain constant region having an amino acid sequence set forth in, e.g., SEQ ID NO: 97, or mouse IgG1 heavy chain constant region having an amino acid sequence set forth in, e.g., 129, and the light chain constant region for all clones may be kappa constant region, such as human kappa constant region having an amino acid sequence set forth in, e.g., SEQ ID NOs: 98, or mouse kappa constant region having an amino acid sequence set forth in, e.g., SEQ ID NO.:130. The antibody Fab may contain heavy/light chain variable region, heavy chain CH1 region (such as the one set forth in SEQ ID NO: 99) and light chain constant region.

TABLE 1

Amino acid sequence ID numbers of heavy/light chain variable regions

| | SEQ ID NO. | | | | | | | |
|---|---|---|---|---|---|---|---|---|
| Clone | VH-CDR1 | VH-CDR2 | VH-CDR3 | VH | VL-CDR1 | VL-CDR2 | VL-CDR3 | VL |
| C1E1 | 1 | 2 | 3 | 67 | 34 | 35 | 36 | 80 |
| huC1E1-V1 | 1 | 2 | 3 | 68 | 34 | 35 | 36 | 81 |
| huC1E1-V2 | 1 | 2 | 3 | 69 | 34 | 35 | 36 | 81 |
| huC1E1-V3 | 1 | 2 | 3 | 68 | 34 | 35 | 36 | 82 |
| huC1E1-V4 | 1 | 2 | 3 | 68 | 34 | 35 | 36 | 83 |
| huC1E1-V5 | 1 | 2 | 3 | 68 | 34 | 35 | 36 | 84 |
| huC1E1-V6 | 1 | 2 | 3 | 68 | 34 | 35 | 36 | 85 |
| huC1E1-V7 | 1 | 2 | 3 | 68 | 34 | 35 | 36 | 86 |
| huC1E1-V10 | 1 | 2 | 3 | 69 | 34 | 35 | 36 | 86 |
| D1F2 | 4 | 5 | 6 | 70 | 37 | 38 | 39 | 87 |
| C1F5 | 7 | 8 | 9 | 71 | 40 | 41 | 42 | 88 |
| D1A1 | 10 | 11 | 12 | 72 | 43 | 44 | 45 | 89 |
| D1F1 | 13 | 14 | 15 | 73 | 46 | 47 | 48 | 90 |
| C1E2 | 16 | 17 | 18 | 74 | 49 | 50 | 51 | 91 |
| C1A1 | 19 | 20 | 21 | 75 | 52 | 53 | 54 | 92 |
| C1F4 | 22 | 23 | 24 | 76 | 55 | 56 | 57 | 93 |
| D2C2 | 25 | 26 | 27 | 77 | 58 | 59 | 60 | 94 |
| 2G2 | 28 | 29 | 30 | 78 | 61 | 62 | 63 | 95 |
| C1C5 | 31 | 32 | 33 | 79 | 64 | 65 | 66 | 96 |

The heavy chain variable region CDRs and the light chain variable region CDRs in Table 1 have been defined by the IMGT numbering scheme and Kabat numbering system, respectively. However, as is well known in the art, CDR regions can also be determined by other systems such as Chothia, and CCG system/method, based on heavy chain/light chain variable region sequences.

The $V_H$ and $V_L$ sequences (or CDR sequences) of other anti-PD-1 antibodies which bind to human PD-1 can be "mixed and matched" with the $V_H$ and $V_L$ sequences (or CDR sequences) of the anti-PD-1 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:

(a) a heavy chain variable region comprising an amino acid sequence listed above in Table 1; and (b) a light chain variable region comprising an amino acid sequence listed above in Table 1, or the $V_L$ of another anti-PD-1 antibody, wherein the antibody specifically binds human PD-1.

In another embodiment, an antibody of the invention, or an antigen binding portion thereof, comprises:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-PD-1 antibody, wherein the antibody specifically binds human PD-1.

In yet another embodiment, the antibody, or antigen binding portion thereof, includes the heavy chain variable CDR2 region of anti-PD-1 antibody combined with CDRs of other antibodies which bind human PD-1, e.g., CDR1 and/or CDR3 from the heavy chain variable region, and/or CDR1, CDR2, and/or CDR3 from the light chain variable region of a different anti-PD-1 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J of Cancer* 83(2):252-260 (2000); Beiboer et al., *J Mol. Biol.* 296:833-849 (2000); Rader et al., *Proc. Natl. Acad. Sci. U.S.A.* 95:8910-8915 (1998); Barbas et al., *J Am. Chem.* Soc. 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: Scientific Review 8 (2001); Igarashi et al., *J. Biochem* (Tokyo) 117:452-7 (1995); Bourgeois et al., J. Virol 72:807-10 (1998); Levi et al., *Proc. Natl. Acad. Sci. U.S.A.* 90:4374-8 (1993); Polymenis and Stoller, *J Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of the anti-PD-1 antibody and at least the CDR3 of the heavy and/or light chain variable region of the anti-PD-1 antibody, or the CDR3 of the heavy and/or light chain variable region of another anti-PD-1 antibody, wherein the antibody is capable of specifically binding to human PD-1. These antibodies preferably (a) compete for binding with PD-1; (b) retain the functional characteristics; (c) bind to the same epitope; and/or (d) have a similar binding affinity as the anti-PD-1 antibody of the present invention. In yet another embodiment, the antibodies further may comprise the CDR2 of the light chain variable region of the anti-PD-1 antibody, or the CDR2 of the light chain variable region of another anti-PD-1 antibody, wherein the antibody is capable of specifically binding to human PD-1. In another embodiment, the antibodies of the invention may include the CDR1 of the heavy and/or light chain variable region of the anti-PD-1 antibody, or the CDR1 of the heavy and/or light chain variable region of another anti-PD-1 antibody, wherein the antibody is capable of specifically binding to human PD-1.

Conservative Modifications

In another embodiment, an antibody of the invention comprises a heavy and/or light chain variable region sequences of CDR1, CDR2 and CDR3 sequences which differ from those of the anti-PD-1 antibodies of the present invention by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol.* Chem. 272:26864-26870; Hall et al., (1992) *J Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof, and/or (b) the heavy chain variable region CDR2 sequence comprises a sequence listed in Table 1 above, and/or conservative modifications thereof, and/or (c) the heavy chain variable region CDR3 sequence comprises a sequence listed in Table 1 above, and conservative modifications thereof, and/or (d) the light chain variable region CDR1, and/or CDR2, and/or CDR3 sequences comprise the sequence(s) listed in Table 1 above; and/or conservative modifications thereof, and (e) the antibody specifically binds human PD-1.

The antibody of the present invention possesses one or more of the following functional properties described above, such as high affinity binding to human PD-1, and the ability to induce ADCC or CDC against PD-1-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-PD-1 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad. See also U.S.A.* 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database, as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-PD-1 monoclonal antibodies, or antigen binding portions thereof, comprising a heavy chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (f) a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) *J. Biol. Chem.* 277: 26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application corresponding to Alston & Bird LLP, filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N—X—S/T sequence. In some instances, it is preferred to have an anti-PD-1 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-PD-1 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the PD-1 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasm, (1980) *Proc. Nat. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-PD-1 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, PD-1, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, Bioconjugate Chemistry, 9 (6), 635-644 (1998); and van Spriel et al., *Immunology Today,* 21 (8), 391-397 (2000), and the references cited therein.

Antibody-Encoding or Antibody-Bearing Oncolytic Virus

An oncolytic virus preferabtially infects and kills cancer cells. Antibodies of the present invention can be used in conjunction with oncolytic viruses. Alternatively, oncolytic viruses encoding antibodies of the present invention can be introduced into human body.

Pharmaceutical Compositions

In another aspect, the present disclosure provides a pharmaceutical composition comprising one or more antibodies of the present invention formulated together with a pharmaceutically acceptable carrier. The antibodies can be dosed separately when the composition contains more than one antibody. The composition may optionally contain one or more additional pharmaceutically active ingredients, such as another antibody or a drug, such as an anti-tumor drug.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-PD-1 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the invention can be formulated to ensure proper distribution in vivo. For example, to ensure that the therapeutic antibody of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J Clin. Pharmacol.* 29:685; Umezawa et al., (1988) *Biochem. Biophys. Res.* Commun. 153:1038; Bloeman et al., (1995) FEBS Lett. 357:140; M. Owais et al., (1995) *Antimicrob. Agents Chemother.* 39:180; Briscoe et al., (1995)*Am. J. Physiol.* 1233:134; Schreier et al., (1994) *J. Biol. Chem.* 269:9090; Keinanen and Laukkanen (1994) *FEBSLett.* 346:123; and Killion and Fidler (1994) *Immunomethods* 4:273.

Uses and Methods of the Invention

Antibodies (compositions, bispecifics, immunoconjugates, and other modalities including oncolytic viruses) of the present invention have numerous in vitro and in vivo utilities involving, for example, enhancement of immune responses by blockade of PD-1. The antibodies can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-PD-1 antibodies can be administered together with an antigen of interest or the antigen may already be present in the subject to be treated (e.g., a tumor-bearing or virus-bearing subject). When antibodies to PD-1 are administered together with another agents, they can be administered in either order or simultaneously.

Given the ability of anti-PD-1 antibodies of the invention to inhibit the binding of PD-1 to PD-L1 and/or PD-L2 molecules and to stimulate antigen-specific T cell responses, the invention also provides in vitro and in vivo methods of using the antibodies to stimulate, enhance or upregulate antigen-specific T cell responses. For example, the invention provides a method of stimulating an antigen-specific T cell response comprising contacting said T cell with an antibody of the invention, such that an antigen-specific T cell response is stimulated. Any suitable indicator of an antigen-specific T cell response can be used to measure the antigen-specific T cell response.

Non-limiting examples of such suitable indicators include increased T cell proliferation in the presence of the antibody and/or increase cytokine production in the presence of the antibody. In a preferred embodiment, interleukin-2 production by the antigen-specific T cell is stimulated.

The invention also provides method for stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another embodiment, the invention provides methods for inhibiting growth of tumor cells in a subject comprising administering to the subject an antibody of the invention such that growth of the tumor is inhibited in the subject. In yet another embodiment, the invention provides methods for treating a viral infection in a subject comprising administering to the subject an antibody of the invention such that the viral infection is treated in the subject.

These and other methods of the invention are discussed in further detail below.

Cancer

Blockade of PD-1 by antibodies can enhance the immune response to cancerous cells in the patient. In one aspect, the present invention relates to treatment of a subject in vivo using an anti-PD-1 antibody such that growth of cancerous tumors is inhibited. An anti-PD-1 antibody can be used alone to inhibit the growth of cancerous tumors. Alternatively, an anti-PD-1 antibody can be used in conjunction with other immunogenic agents used in cancer treatments such as oncolytic viruses, or other antibodies, as described below.

Accordingly, in one embodiment, the invention provides a method of inhibiting growth of tumor cells in a subject, comprising administering to the subject a therapeutically effective amount of an anti-PD-1 antibody, or antigen-binding portion thereof. Preferably, the antibody is a mouse, chimeric or humanized anti-PD-1 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer), whether original or metastatic. Additionally, the invention includes refractory or recurrent malignancies whose growth may be inhibited using the antibodies of the invention.

Examples of other cancers that can be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-1 (Iwai et al. (2005) *Int. Immunol.* 17:133-144).

Optionally, antibodies to PD-1 can be combined with an immunogenic agents, such as cancerous cells, purified tumor antigens (including recombinant proteins, peptides, and carbohydrate molecules), and cells transfected with genes encoding immune stimulating cytokines (He et al (2004) *J Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

PD-1 blockade is likely to be more effective when combined with a vaccination protocol. Many experimental strategies for vaccination against tumors have been devised (see Rosenberg, S., 2000*, Development of Cancer Vaccines*, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., *Cancer Vaccines*, Ch. 61, pp. 3023-3043 in DeVita et al. (eds.), 1997*, Cancer: Principles and Practice of Oncology*, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The study of gene expression and large scale gene expression patterns in various tumors has led to the definition of so called tumor specific antigens (Rosenberg, SA (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-1 blockade can be used in conjunction with a collection of recombinant proteins and/or peptides expressed in a tumor in order to generate an immune response to these proteins. These proteins are normally viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). These somatic tissues may be protected from immune attack by various means. Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with PD-1 blockade to activate more potent anti-tumor responses.

PD-1 blockade can also be combined with standard cancer treatments. PD-1 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-PD-1 antibody in combination with decarbazine for the treatment of melanoma. Another example of such a combination is an anti-PD-1 antibody in combination with interleukin-2 (IL-2) for the treatment of melanoma. The scientific rationale behind the combined use of PD-1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors can also be combined with PD-1 blockade. Inhibition of angiogenesis leads to tumor cell death which may feed tumor antigen into host antigen presentation pathways.

PD-1 blocking antibodies can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example, anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-PD-1 to counteract the effects of the immunosuppressive agent and favor tumor immune responses by the host.

Other antibodies which activate host immune responsiveness can be used in combination with anti-PD-1. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with PD-1 antibodies (Ito et al. (2000) *Immunobiology* 201 (5) 527-40). Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997)

*Nature Medicine* 3: 682-685 (1997), and ICOS (Hutloff et al. (1999) *Nature* 397: 262-266) may also provide for increased levels of T cell activation.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-PD-1 antibodies can increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-1 antibody, or antigen-binding portion thereof, such that the subject is treated for the infectious disease. Preferably, the antibody is a chimeric or humanized antibody.

Similar to its application to tumors as discussed above, antibody mediated PD-1 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. PD-1 blockade is particularly useful against established infections by agents such as HIV that present altered antigens over the course of the infections. These novel epitopes are recognized as foreign at the time of anti-human PD-1 administration, thus provoking a strong T cell response that is not dampened by negative signals through PD-1.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia*, rickettsial bacteria, mycobacteria, staphylococci, streptococci, pneumonococci, meningococci and gonococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus Mucorales (*mucor, absidia, rhizopus*), *Sporothrix schenkii, Blastomyces dermatitidis, Paracoccidioides brasiliensis, Coccidioides immitis* and *Histoplasma capsulatum.*

Some examples of pathogenic parasites causing infections treatable by methods of the invention include *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis.*

In all of the above methods, PD-1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natd. Acad. Sci. USA* 90:6444-6448; Poljak (1994) *Structure* 2:1121-1123).

Autoimmune Reactions

Anti-PD-1 antibodies may provoke and amplify autoimmune responses. Indeed, induction of anti-tumor responses using tumor cell and peptide vaccines reveals that many anti-tumor responses involve anti-self reactivities (van Elsas et al. (2001) *J. Exp. Med.* 194:481-489; Overwijk, et al. (1999) *Proc. Natd. Acad. Sci. U.S.A.* 96: 2982-2987; Hurwitz, (2000) supra; Rosenberg & White (1996) *J Immunother Emphasis Tumor Immunol* 19 (1): 81-4). Therefore, it is possible to consider using anti-PD-1 blockade in conjunction with various self-proteins in order to devise vaccination protocols to efficiently generate immune responses against these self-proteins for disease treatment.

Other self-proteins can also be used as targets such as IgE for the treatment of allergy and asthma, and TNFα for rheumatoid arthritis. Finally, antibody responses to various hormones may be induced by the use of anti-PD-1 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-PD-1 antibody can be used for induction of therapeutic autoimmune responses to treat patients having an inappropriate accumulation of other self-antigens, such as cytokines such as TNFα, and IgE.

Combination Therapy

In another aspect, the invention provides methods of combination therapy in which an anti-PD-1 antibody (or antigen-binding portion thereof) of the present invention is co-administered with one or more additional antibodies that are effective in stimulating immune responses to thereby further enhance, stimulate or upregulate immune responses in a subject. In one embodiment, the invention provides a method for stimulating an immune response in a subject comprising administering to the subject an anti-PD-1 antibody and one or more additional immune-stimulatory antibodies, such as an anti-LAG-3 antibody, an anti-PD-L1 antibody and/or an anti-CTLA-4 antibody, such that an immune response is stimulated in the subject, for example to inhibit tumor growth or to stimulate an anti-viral response. In another embodiment, the subject is administered an anti-PD-1 antibody and an anti-LAG-3 antibody. In still another embodiment, the subject is administered an anti-PD-1 antibody and an anti-PD-L1 antibody. In yet another embodiment, the subject is administered an anti-PD-1 antibody and an anti-CTLA-4 antibody. In another embodiment, the at least one additional immune-stimulatory antibody (e.g., anti-PD-1, anti-PD-L1 and/or anti-CTLA-4 antibody) is a human antibody. Alternatively, the at least one additional immune-stimulatory antibody can be, for example, a chimeric or humanized antibody (e.g., prepared from a mouse anti-LAG-3, anti-PD-L1 and/or anti-CTLA-4 antibody).

In another embodiment, the invention provides a method for treating a hyperproliferative disease (e.g., cancer), comprising administering a PD-1 antibody and a CTLA-4 antibody to a subject. In further embodiments, the anti-PD-1 antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-PD-1 antibody and a subtherapeutic dose of anti-CTLA-4 antibody to a subject. In certain embodiments, the subject is human. In other embodiments, the anti-CTLA-4 antibody is human sequence monoclonal antibody 10D1 (described in PCT Publication WO 01/14424) and the anti-PD-1 antibody is mouse sequence monoclonal antibody, such as anti-PD-1 antibody C1H5 described herein. Other anti-CTLA-4 antibodies encompassed by the methods of the present invention include, for example, those disclosed in: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J Clin. Oncology* 22(145): Abstract No. 2505 (antibody CP-675206); and Mokyr et al. (1998) *Cancer Res.* 58:5301-5304. In certain embodiments, the anti-CTLA-4 antibody binds to human CTLA-4 with a $K_D$ of $5\times10^{-8}$ M or less, binds to human CTLA-4 with a $K_D$ of $1\times10^{-8}$ M or less, binds to human CTLA-4 with a $K_D$ of $5\times10^{-9}$ M or less, or binds to human CTLA-4 with a $K_D$ of between $1\times10^{-8}$ M and $1\times10^{-10}$ M or less.

In another embodiment, the present invention provides a method for treating a hyperproliferative disease (e.g., cancer), comprising administering an anti-PD-1 antibody and an anti-LAG-3 antibody to a subject.

In another embodiment, the present invention provides a method for treating a hyperproliferative disease (e.g., cancer), comprising administering an anti-PD-1 antibody and an anti-PD-L1 antibody to a subject.

Blockade of PD-1 and one or more second target antigens such as CTLA-4 and/or LAG-3 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-PD-1 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J Exp. Med.* 163: 1037-1050), IL-10 (Howard & O'Garra (1992) *Immunology Today* 13: 198-200), and Fas ligand (Hahne et al. (1996) *Science* 274: 1363-1365). In another example, antibodies to each of these entities can be further combined with an anti-PD-1 and anti-CTLA-4 and/or anti-LAG-3 and/or anti-PD-L1 antibody combination to counteract the effects of immunosuppressive agents and favor anti-tumor immune responses by the host.

Other antibodies that can be used to activate host immune responsiveness can be further used in combination with an anti-PD-1 and anti-CTLA-4 and/or anti-LAG-3 and/or anti-PD-L1 antibody combination. These include molecules on the surface of dendritic cells that activate DC function and antigen presentation. Anti-CD40 antibodies (Ridge et al., supra) can be used in conjunction with an anti-PD-1 and anti-CTLA-4 and/or anti-LAG-3 and/or anti-PD-L1 combination (Ito et al., supra). Other activating antibodies to T cell costimulatory molecules (Weinberg et al., supra, Melero et al. supra, Hutloff et al., supra) may also provide for increased levels of T cell activation.

As discussed above, bone marrow transplantation is currently being used to treat a variety of tumors of hematopoietic origin. A combined PD-1 and CTLA-4 and/or LAG-3 and/or PD-L1 blockade can be used to increase the effectiveness of the donor engrafted tumor specific T cells.

Several experimental treatment protocols involve ex vivo activation and expansion of antigen specific T cells and adoptive transfer of these cells into recipients of antigen-specific T cells against tumor (Greenberg & Riddell, supra). These methods can also be used to activate T cell responses to infectious agents such as CMV. Ex vivo activation in the presence of anti-PD-1 and anti-CTLA-4 and/or anti-LAG-3 and/or anti-PD-L1 antibodies can be expected to increase the frequency and activity of the adoptively transferred T cells.

In certain embodiments, the present invention provides a method for altering an adverse event associated with treatment of a hyperproliferative disease (e.g., cancer) with an immunostimulatory agent, comprising administering an anti-PD-1 antibody and a subtherapeutic dose of anti-CTLA-4 and/or anti-LAG-3 and/or anti-PD-L1 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination of PD-1 with CTLA-4 and/or LAG-3 and/or PD-L1 blockade (i.e., immunostimulatory therapeutic antibodies anti-PD-1 and anti-CTLA-4 and/or anti-LAG-3 antibodies and/or anti-PD-L1 antibodies) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC™ (Astra-Zeneca) is a pH- and time-dependent oral formulation of budesonide developed to optimize drug delivery to the ileum and throughout the colon. ENTOCORT EC™ is approved in the U.S. for the treatment of mild to moderate Crohn's disease involving the ileum and/or ascending colon. The usual oral dosage of ENTOCORT EC™ for the treatment of Crohn's disease is 6 to 9 mg/day. ENTOCORT EC™ is released in the intestines before being absorbed and retained in the gut mucosa. Once it passes through the gut mucosa target tissue, ENTOCORT EC™ is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC™ can result in systemic glucocorticoid effects such as hypercorticism and adrenal suppression. See PDR $58^{th}$ ed. 2004; 608-610.

In still further embodiments, a combination of PD-1 with CTLA-4 and/or LAG-3 and/or PD-L1 blockade (i.e., immunostimulatory therapeutic antibodies anti-PD-1 and anti-CTLA-4 and/or anti-LAG-3 and/or anti-PD-L1 antibodies) in conjunction with a non-absorbable steroid can be further combined with a salicylate. Salicylates include 5-ASA agents such as, for example: sulfasalazine (AZULFIDINE™, Pharmacia & UpJohn); olsalazine (DIPENTUM™, Pharmacia & UpJohn); balsalazide (COLAZAL™, Salix Pharmaceuticals, Inc.); and mesalamine (ASACOL™, Procter & Gamble Pharmaceuticals; PENTASA™, Shire US; CANASA™, Axcan Scandipharm, Inc.; ROWASA™, Solvay).

In accordance with the methods of the present invention, a salicylate administered in combination with anti-PD-1 and anti-CTLA-4 and/or anti-LAG-3 and/or anti-PD-L1 antibodies and a non-absorbable steroid can include any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the combination of anti-PD-1 with anti-CTLA-4 and/or anti-LAG-3 and/or anti-PD-L1 antibodies.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-PD-1 Monoclonal Antibodies Using Hybridoma Technology Immunization Mice were immunized according to the method as described in E Harlow, D. Lane, Antibody: *A Laboratory Manual*, Cold Spring Harbor Laboratory Press, Cold Spring Harbor, N.Y., 1998. Recombinant human PD-1 protein with human IgG1 Fc tag at the C-terminus (Acro biosystems, #PD-1-H5257, containing extra-cellular domain, AA Leu 25—Gln 167) was used as the immunogen. Human PD-1-his protein (Sino biological, #10377-H08H) was used for determining anti-sera titer and for screening hybridomas secreting antigen-specific antibodies.

In specific, each animal was injected with 25 μg human PD1 Fc protein in complete Freud's adjuvant (Sigma, St. Louis, Mo., USA), and then boosted for 2 to 3 times by injection of 25 μg human PD1 Fc protein in noncomplete Freud's adjuvant (Sigma, St. Louis, Mo., USA) depending on the anti-sera titer. The anti-sera titer was measured by ELISA-based screening using recombinant human PD1-his protein. Briefly, diluted sera (60 μl) was added to each well and incubated at 37° C. for 40 minutes. Plates were then washed 4 times, HRP-goat anti-mouse-IgG (Jackson Immuno research, Cat #115-036-071) was used for detection, and binding ODs were observed at 450 nm. Animals with good titers were given a final boost by intraperitoneal injection before hybridoma fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," *Nature,* 256: 495-497(1975). Fused "hybrid cells" were subsequently dispensed into 96-well plates in DMEM/20% FCS/HAT media. Surviving hybridoma colonies were observed under the microscope seven to ten days post fusion. After two weeks, the supernatant from each well was subjected to ELISA-based screening using recombinant human PD1-his protein. Briefly, ELISA plates were coated with 60 μl of human PD1-his (Sino biological, #10377-H08H, 2.0 μg/ml in PBS) overnight at 4° C. Plates were washed 4 times with PBST and blocked with 200 μl blocking buffer (5% non-fatty milk in PBST). Diluted hybridoma supernatant (60 μl) was added to each well and incubated at 37° C. for 40 minutes. Plates were then washed 4 times, HRP-goat anti-mouse-IgG (Jackson Immuno research, Cat #115-036-071) was used for detection, and binding ODs were observed at 450 nm. Positive hybridoma secreting antibody that binds to human PD1-his were then selected and transferred to 24-well plates. Hybridoma clones producing antibodies that showed high specific binding and PD1/PDL1 blocking activity were subcloned, and antibodies produced by the subclones were purified by protein A affinity chromatography. Briefly, Protein A sepharose column (from bestchrom(Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing IgG were pooled and dialyzed in PBS overnight at 4° C.

Example 2 Affinity Determination of Mouse Anti-PD-1 Monoclonal Antibodies Using BIACORE Surface Plasmon Resonance Technology The purified anti-PD-1 mouse monoclonal antibodies (mAbs) generated in Example 1, namely clone C1E1, D1F2, C1F5, D1A1, D1F1, C1E2, C1A1, C1F4, D2C2, 2G2, and C1C5, all determined later to be IgG1/kappa isotype, were characterized for affinities and binding kinetics by Biacore T200 system (GE healthcare, Pittsburgh, PA, USA).

Briefly, goat anti-mouse IgG (GE healthcare, Cat #BR100839, Human Antibody Capture Kit) was covalently linked to a CM5 chip (carboxy methyl dextran coated chip) via primary amines, using a standard amine coupling kit (GE healthcare, Pittsburgh, PA, USA) provided by Biacore. Unreacted moieties on the biosensor surface were blocked with ethanolamine. Then purified anti-PD-1 antibodies and Nivolumab (OPDIVO®) at the concentration of 66.7 nM were flowed onto the chip at a flow rate of 10 μL/min. Then, recombinant human PD-1-his (Sino biological, #10377-H08H) or cynomolgus monkey PD-1-his protein (Acro biosystems, #PD-1-C5223) in HBS EP buffer (provided by Biacore) was flowed onto the chip at a flow rate of 30 μL/min. The antigen-antibody association kinetics was followed for 2 minutes and the dissociation kinetics was followed for 10 minutes. The association and dissociation curves were fit to a 1:1 *Langmuir* binding model using BIA evaluation software.

The $k_a$, $k_a$ and $K_D$ values were determined and shown in Table 2 below.

TABLE 2

Biacore Kinetics of Mouse Anti-PD-1 Monoclonal Antibodies Binding to Human or Cynomolgus Monkey PD-1

| | Kinetics on Biacore | | | | | |
|---|---|---|---|---|---|---|
| | Human PD-1 | | | Cynomolgus PD-1 | | |
| Clone | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| D1F2 | 1.94E+05 | 2.03E−04 | 1.05E−09 | 2.00E+05 | 0.006324 | 3.17E−08 |
| C1F5 | 3.53E+05 | 1.31E−04 | 3.72E−10 | 1.38E+05 | 0.002489 | 1.81E−08 |
| C1E1 | 1.72E+05 | 5.88E−05 | 3.42E−10 | 2.03E+05 | 7.89E+04 | 3.90E−09 |
| D1A1 | 1.88E+05 | 3.86E−04 | 2.06E−09 | 2.10E+05 | 0.002358 | 1.13E−08 |
| D1F1 | 2.04E+05 | 5.77E−04 | 2.83E−09 | 2.60E+04 | 0.002919 | 1.12E−07 |
| C1E2 | 1.53E+05 | 4.42E−04 | 2.88E−09 | 2.38E+05 | 0.002978 | 1.25E−08 |
| C1A1 | 1.68E+05 | 1.89E−04 | 1.13E−09 | 3.48E+05 | 3.31E−03 | 9.50E−09 |
| C1F4 | 1.56E+05 | 3.59E−04 | 2.30E−09 | 3.01E+05 | 0.005208 | 1.73E−08 |
| D2C2 | 1.73E+05 | 3.07E−04 | 1.77E−09 | 2.06E+04 | 0.00238 | 1.16E−07 |
| 2G2 | 1.63E+05 | 4.36E−04 | 2.68E−09 | 1.40E+05 | 1.83E−03 | 1.30E−08 |
| C1C5 | 2.31E+05 | 2.03E−04 | 8.80E−10 | 3.22E+05 | 4.70E−03 | 1.46E−08 |
| OPDIVO ® | 4.33E+05 | 1.41E−03 | 3.25E−09 | / | / | / |

The antibodies of the present invention bound to human PD-1 specifically with a lower $K_D$ than Nivolumab, indicating higher affinity to human PD-1.

Example 3 Binding Activity of Mouse Anti-PD-1 Monoclonal Antibodies 96-well micro plates were coated with 2 μg/ml goat anti-mouse IgG Fcγ fragment (Jackson Immuno Research, #115-006-071,100 μl/well) in PBS and incubated overnight at 4° C. Plates were washed 4 times with wash buffer (PBS+0.05% Tween-20, PBST) and then blocked with 200 μl/well blocking buffer (5% w/v non-fatty milk in PBST) for 2 hours at 37° C. Plates were washed again and incubated with 100 μl/well purified anti-PD-1 antibodies of Example 1 and Nivolumab (0.004-66.7 nM, 5-fold serial dilution in 2.5% non-fatty milk in PBST) for 40 minutes at 37° C., and then washed 4 times again. Plates containing captured anti-PD-1 antibodies were incubated with biotin-labeled human PD-1 Fc protein (SEQ ID NO: 100, 60 nM in 2.5% non-fatty milk in PBST, 100 μl/well) for 40 minutes at 37° C., washed 4 times, and incubated with streptavidin conjugated HRP (1:10000 dilution in PBST, Jackson Immuno Research, #016-030-084, 100 μl/well) for 40 minutes at 37° C. After a final wash, plates were incubated with 100 μl/well ELISA substrate TMB (Innoreagents). The reaction was stopped in 15 minutes at 25° C. with 50 μl/well 1M $H_2SO_4$, and the absorbance was read at 450 nm. Data were analyzed using Graphpad Prism software and $IC_{50}$ values were reported.

The results were summarized in Table 3 below.

TABLE 3

Binding Activity of anti-PD-1 antibodies to Human PD-1

| Clone | Capture ELISA ($EC_{50}$, nM) |
|---|---|
| D1F2 | 0.19 |
| C1F5 | 0.16 |
| C1E1 | 0.16 |
| D1A1 | 0.2 |
| D1F1 | 0.24 |
| C1E2 | 0.2 |
| C1A1 | 0.18 |
| C1F4 | 0.25 |
| D2C2 | 0.2 |
| 2G2 | 0.18 |
| C1C5 | 0.16 |
| OPDIVO ® | 0.21 |

The result indicated that the antibodies of the present invention bound to human PD-1 specifically, with several clones having lower $IC_{50}$ values than Nivolumab.

Example 4 Functional Blockage Assays Using ELISA and Report Assays 4.1 Ligand Blocking ELISA The ability of anti-PD-1 antibodies of the present invention to block the PD-1-PD-L1 interaction was measured using a competitive ELISA assay. Briefly, human PD-L1-Fc proteins (SEQ ID NO:101) were coated on 96-well micro plates at 2 μg/mL PBS and incubated overnight at 4° C. The next day, plates were washed with wash buffer (PBS+0.05% Tween-20, PBST), and blocked with 5% non-fatty milk in PBST for 2 hours at 37° C. Plates were then washed again using wash buffer.

Dilutions of the anti-PD-1 antibodies of the present invention or Nivolumab (starting at 100 nM with a four-fold serial dilution) in biotin labeled human PD-1-Fc (SEQ ID NO: 100, 10 nM in 2.5% non-fatty milk in PBST) were prepared and incubated at room temperature for 40 minutes, and then the antibodies/PD-1-Fc-biotin mixtures (100 μl/well) were added to PD-L1-coated plates. After incubation at 37° C. for 40 minutes, plates were washed for 4 times using wash buffer. Then 100 μl/well streptavidin conjugated HRP was added and incubated for 40 minutes at 37° C. to detect biotin-labeled human PD-1 bound to PD-L1. Plates were washed again using wash buffer. Finally, TMB was added and the reaction was stopped using 1M $H_2SO_4$, and the absorbance was read at 450 nm. Data were analyzed using Graphpad Prism software and $IC_{50}$ values were reported.

4.2 Benchmark Blocking ELISA

The ability of the anti-PD-1 antibodies of the present invention to block Benchmark (Nivolumab)-human PD-1 binding was measured using a competitive ELISA assay. Briefly, Nivolumab was coated on 96-well micro plates at 2 μg/mL in PBS and incubated overnight at 4° C. The next day, plates were washed with wash buffer, and blocked with 5% non-fatty milk in PBST for 2 hours at 37° C. While blocking, biotin labeled human PD-1 Fc (SEQ ID NO:100, 10 nM in 2.5% non-fatty milk in PBST) was mixed with each of the antibodies to test (137 pM-100 nM, 3-fold serial dilution) and incubated for 40 minutes at 25° C. After washing, the PD-1/antibody mixtures (100 μl/well) were added to plates coated with Nivolumab and incubated for 40 minutes at 37° C. Plates were washed again with wash buffer, and then 100 μl/well SA-HRP was added and incubated for 40 minutes at 37° C. to detect biotin-labeled human PD-1 bound to Opdivo©. Plates were finally washed using wash buffer. TMB was added and the reaction was stopped using 1M $H_2SO_4$, and the absorbance was read at 450 nm. Data were analyzed using Graphpad Prism software and $IC_{50}$ values were reported.

4.3 Cell-Based Functional Assays

The activity of antibodies to block cell membrane PD-1/PD-L1 interaction was evaluated by using a cell-based reporter assay. This assay consisted of two genetically engineered cell lines, PD-1 Effector Cell Line (Genscript, GS-J2/PD-1) stably expressing human PD-1 and a luciferase reporter driven by an NFAT response element (NFAT-RE), and PD-L1 Cell Line (Genscript, GS-C2/PD-L1, APC cells) stably expressing human PD-L1 and an engineered cell surface protein-antigenic peptide/major histocompatibility complex (MHC). When these two cell lines were co-cultured, the T-cell receptor (TCR)-mediated luciferase expression of PD-1 effector cell (via of the NFAT pathway) was inhibited by PD-1/PD-L1 interaction.

The cell-based functional assay was carried out as follows. Briefly, PD-L1 cells at the log phase stage were seeded into 384-well cell culture plates at the density of $5*10^5$/ml. The next day, dilution of anti-PD-1 antibodies of the present invention or Nivolumab (starting from 333.3 nM, 5-fold serial dilution) in assay buffer (RPMI 1640+1% FBS) were prepared. Meanwhile, the media of PD-L1 cells in 384-well plates were discarded, and then the dilutions of anti-PD-1 antibodies (20 μl/well) and PD-1 effector cells (at the density of $6.25*10^5$/ml, 20 μl/well) were added to 384-well cell culture plates. After co-cultured at 37° C. for six hours, the plates were removed from the incubator and the luminescence of each well was read according to the manufacturer's instructions with One-Glo Luciferase Assay system (Promega, #E6120). The dose-response curves were analyzed using Graphpad Prism software and $IC_{50}$ values were reported.

The results of the three assays were summarized in Table 4 below.

TABLE 4

Anti-PD-1 antibodies' Capacity for Blocking PD-1/PD-L1 interaction

| Clone | Functional Blockage Assays Competition ELISA ($IC_{50}$, nM) human PD-1/ human PD-L1 | Functional Blockage Assays Competition ELISA ($IC_{50}$, nM) Opdivo®/ human PD-1 | Reporter Activation ($EC_{50}$, nM) human PD-1 cell (NFAT-luc)/ human PD-L1 cell |
|---|---|---|---|
| D1F2 | 0.21 | 1.4 | 7.349 |
| C1F5 | 0.21 | 0.87 | 7.579 |
| C1E1 | 0.26 | 1.1 | 9.114 |
| D1A1 | 0.22 | 1.28 | 9.128 |
| D1F1 | 0.2 | 2.13 | 10.84 |
| C1E2 | 0.25 | 1.49 | 11.13 |
| C1A1 | 0.27 | 1.4 | 12.14 |
| C1F4 | 0.43 | 2.26 | 13.24 |
| D2C2 | 0.21 | 1.89 | 14.67 |
| 2G2 | 0.32 | 14.45 | 17.86 |
| C1C5 | 0.23 | 1.34 | 23.36 |
| OPDIVO ® | 0.12 | 3.79 | 13.62 |

It can be seen that the antibodies of the present invention were capable of blocking human PD-1/human PD-L1 interaction, with several clones having lower $IC_{50}$ or $IC_{50}$ values than Nivolumab.

The data also showed that the antibodies of the present invention were able to block human PD-1/Nivolumab interaction, wherein antibodies from Clone 2G2 had partial blocking, indicating they bound to the same or similar epitope as Nivolumab did.

Example 5 Generation and Characterization of Chimeric Antibodies

The variable domains of the heavy and light chain of the anti-PD1 mouse mAb C1E1 were cloned in frame to human IgG1 heavy-chain and human kappa light-chain constant regions, respectively. The heavy chain variable region and the light chain variable region had amino acid sequences set forth in SEQ ID NOs.: 67 and 80, respectively, while the amino acid sequences of the human IgG1 heavy-chain and human kappa light-chain constant regions were set forth in SEQ ID NOs.: 97 and 98, respectively. The activities of the resulting chimeric antibodies were confirmed in binding capture ELISA, competition ELISA and cell-based functional reporter assay following the protocols in the foregoing Examples. The data showed that the chimeric C1E1 antibody had activities comparable to those of the benchmark (OPDIVO®), as shown in Table 5 below.

TABLE 5

| Binding and functional activities of Chimeric Antibodies | | | | |
|---|---|---|---|---|
| Clone ID# | Capture binding ELISA ($EC_{50}$, nM) | PD1/PDL1 ligand blocking ELISA ($IC_{50}$, nM) | Benchmark blocking ELISA ($IC_{50}$, nM) | Cell-based functional reporter assay ($IC_{50}$, nM) |
| Chimeric C1E1 | 0.23 | 0.53 | 0.20 | 8.53 |
| OPDIVO ® | 0.37 | 0.41 | 0.38 | 10.32 |

Example 6 Humanization of Anti-PD-1 Mouse Monoclonal Antibody C1E1

Mouse anti-PD1 antibody C1E1 was selected for humanization and further investigations. Humanization of the mouse antibody was conducted using the well-established CDR-grafting method as described in detail below.

To select acceptor frameworks for humanization of mouse antibody C1E1, the light and heavy chain variable region sequences of mouse C1E1 were blasted against the human immunoglobulin gene database. The human germline IGVH and IGVK with the highest homology to mouse C1E1 were selected as the acceptor frameworks for humanization. The mouse antibody heavy/light chain variable region CDRs were inserted the selected frameworks, and the residue(s) in the frameworks was/were further mutated to obtain more candidate heavy chain/light chain variable regions.

The vectors containing nucleotide sequences encoding humanized C1E1 heavy chain/light chain variable regions and human IgG1 heavy-chain and human kappa light-chain constant regions were transiently transfected into 50 ml of 293F suspension cell cultures in a ratio of 60% to 40% light to heavy chain construct, with 1.2 mg/ml PEI. Cell supernatants were harvested after six days in shaking flasks, spun down to pellet cells, and filtered through 0.22 μm filters before IgG separation. The antibodies were purified by protein A affinity chromatography. Briefly, Protein A sepharose column (from bestchrom (Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing IgG were pooled and dialyzed in PBS overnight at 4° C.

A total of 10 humanized antibodies were obtained, 8 of which were further characterized, namely from huC1E1-V1 to huC1E1-V7 and huC1E1-V10. The heavy chain/light chain variable region amino acid sequences of the 8 antibodies were summarized in Table 1 above, and the human IgG1 heavy-chain and human kappa light-chain constant region sequences were set forth in SEQ ID NOs.: 97 and 98, respectively.

The binding affinity of huC1E1-V1 to huC1E1-V7 to human PD1 were assessed by the BIACORE technology as described in Example 2, and the affinities $K_D$ values were summarized in Table 6 below. Antibody huC1E1-V10 was assessed for its binding activity to human PD1 through a capture binding ELISA as describe in Example 3, which utilized a goat anti-human IgG Fab capture antibody (Jackson ImmunoResearch, Cat #109-005-097) to capture IgG, and the binding $IC_{50}$ values were summarized in Table 7. All 8 humanized antibodies had comparable affinities to the chimeric antibody C1E1.

TABLE 6

| Affinities of Humanized C1E1 mAbs | |
|---|---|
| mAb | Human PD1 Biacore (KD, M) |
| huC1E1-V1 | 3.88E−09 |
| huC1E1-V2 | 2.49E−09 |
| huC1E1-V3 | 4.52E−09 |
| huC1E1-V4 | 2.95E−09 |
| huC1E1-V5 | 3.37E−09 |
| huC1E1-V6 | 3.05E−09 |
| huC1E1-V7 | 6.36E−09 |
| huC1E1-V10 | 9.68E−10 |
| Chimeric C1E1 | 1.83E−09 |
| OPDIVO ® | 1.49E−08 |

TABLE 7

| Binding Activities of Humanized C1E1 mAb | |
|---|---|
| mAb | Human PD1 Binding capture ELISA ($E_{C50}$, nM) |
| huC1E1-V10 | 0.44 |
| Chimeric C1E1 | 0.16 |
| OPDIVO ® | 1.19 |

The humanized antibody huC1E1-V10 was then tested for the affinity for human and cynomolgus PD1 by Biacore and by binding capture ELISA, and also tested for the functional activities by competition ELISA and by cell-based reporter assay, following the protocols in Examples 2 to 4. As showed in Table 8, huC1E1-V10 showed comparable in vitro activities to the chimeric C1E1 antibody.

TABLE 8

Binding and Functional activities of Humanized C1E1 mAb Summary of

| mAbs | Binding assay: Human PD1 Binding ELISA ($EC_{50}$, nM) | Binding assay: Human PD1 Biacore (KD, M) | Binding assay: Cynomolgus PD1 Biacore (KD, M) | Functional assay: Competition ELISA ($IC_{50}$, nM) PD1/PDL 1 ligand blocking ELISA | Functional assay: Competition ELISA ($IC_{50}$, nM) Benchmark blocking ELISA | Functional assay: Cell-based reporter assay ($EC_{50}$, nM) |
|---|---|---|---|---|---|---|
| huC1E1-V10 | 0.34 | 9.68E−10 | 8.92E−10 | 0.88 | 0.35 | 11.26 |
| chC1E1 | 0.23 | 8.81E−10 | 8.45E−10 | 0.53 | 0.20 | 8.53 |
| OPDIVO ® | 0.37 | 8.17−09 | 1.40E−08 | 0.41 | 0.38 | 10.32 |

Example 7 Physicochemical Properties of Humanized C1E1 Antibody

Physicochemical Properties of the anti-PD1 humanized antibody huC1E1-V10 were examined by using Protein Thermal Shift assay, cIEF Technique, SEC Technique and Freeze-Thaw Method as described below.

Protein Thermal Shift Assay to Determine Tm

The thermal stability of the anti-PD1 humanized antibody huC1E1-V10 was measured using a GloMelt™ Thermal Shift Protein Stability Kit (Biotium, Cat #33022-T, lot #: 181214). Briefly, GloMelt™ dye was allowed to thaw and reach room temperature. The vial containing the dye was vortexed and centrifuged. 10× dye was prepared by adding 5 μL 200× dye to 95 μL PBS. 2 μL 10× dye and 10 μg antibody were added in a total 20 μL reaction volume. The run of a melt curve program having detailed parameters in Table 9 was set up. Tubes were spun briefly and placed in real-time PCR thermocycler (Roche, LightCycler 480 II). The results were analyzed using Microsoft Excel 2010 software.

TABLE 9

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA |

cIEF Technique to Determine pI

Capillary isoelectric focusing (cIEF) was used to determine the pI and charge heterogeneity of the anti-PD1 humanized antibody huC1E1-V10. Briefly, 35 μL 0.1% MC, 4 μL pH3-10 Pharmlyte, 2 μL 0.5 mol/L Arg, 1 μL Mark-7.05 and 1 μL Mark-9.99 were added to a tube containing 20 μg antibody in PBS, then $ddH_2O$ was added up to 100 μL. The electrophoresis program consisted of two phases: initial separation for 1 minute at 1500 V followed by 6 minutes at 3000 V. After 5 min exposures for detection, data were analyzed using Maurice™Compass™ software (Proteinsimple Inc., USA).

SEC Technique to Determine Aggregation

The percentage of monomer was assessed with size exclusion chromatography (SEC) (Agilent Technologies, 1260 Infinity II). Antibodies were carried in an aqueous mobile phase and passed through a porous stationary phase resin packed in a column. The retention time in the column was a function of the hydrodynamic size of the protein and the size of the pores in the packed resin bed. Smaller molecules can penetrate into smaller pores in the resin and were retained longer than larger molecules. Upon elution from the column, the proteins were detected by UV absorbance. The mobile phase was a phosphate-buffered saline solution and the absorbance was monitored at 280 nm. The flow rate was 0.8 mL/minute. Injection volume was 40 μL of 1 mg/mL sample. The column temperature was room temperature. The auto-sampler temperature was 2-8° C. The total run time was 25 minutes.

Freeze-Thaw Method to Determine Stability

Antibody solutions at 1 mg/ml in 1xPBS formulation(s) (containing 137 mmol/L NaCl, 2.7 mmol/L KCl, 10 mmol/L $Na_2HPO_4.12H_2O$, 2 mmol/L $KH_2PO_4$) were frozen at −80° C. for at least 24 hours and then thawed at room temperature for 30-60 minutes. The freeze and thaw cycle was repeated 5 times for each sample. After certain freeze-thaw cycles, e.g., second, third and fourth, a portion of the solution was withdrawn for analysis by SEC before refreezing.

Figure 2:
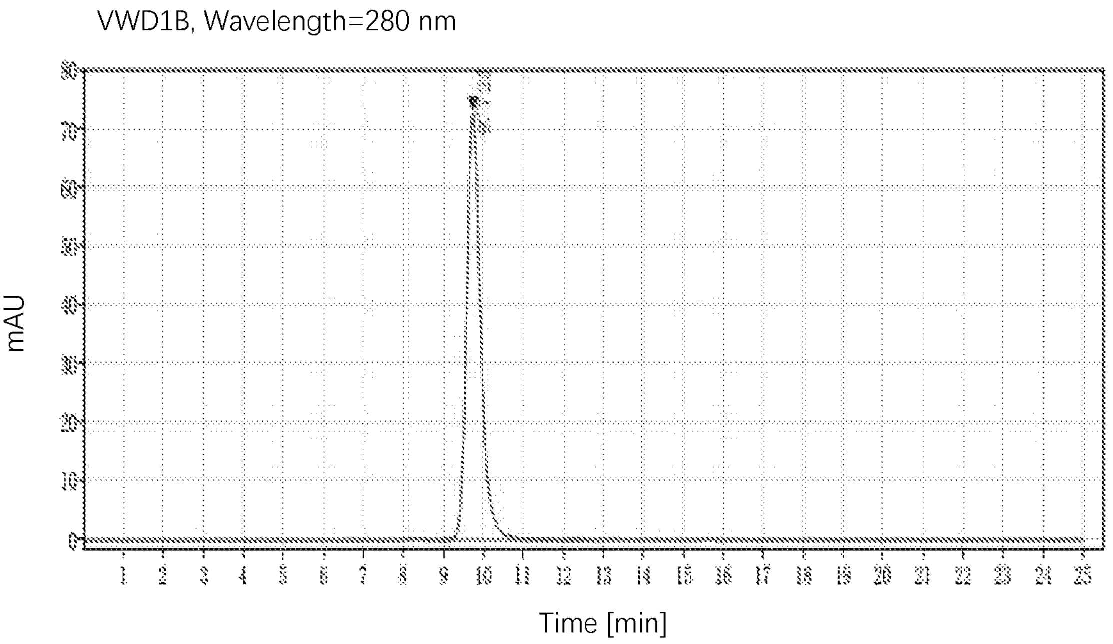
FIG. 2 shows the result of size exclusion chromatography of humanized anti-PD-1 antibody huC1E1-V10.

Instability leading to denaturation was assessed by a GloMelt™ Thermal Shift Protein Stability Kit. As shown in FIG. 1, anti-PD1 humanized antibody huC1E1-V10 showed high melting temperature (Tm) typically at 78° C. and also a minor peak at 69.5° C. The cIEF assay for huC1E1-V10 indicated that the % Major Isoform was about 81.5%, the % Acidic Species was about 11.0% and the % Basic Species was about 7.5%. The pIs were calculated using Maurice™Compass™software, and the pI value of huC1E1-V10 antibody was 8.36. The huC1E1-V10 humanized antibody had a pI significantly above 7 and therefore expected to have a significant positive charge at neutral pH. SEC test for huC1E1-V10 indicated that the % Monomer was 100.0% (see FIG. 2). Stability to freezing and thawing was assessed by size exclusion chromatography (SEC). Antibody huC1E1-V10 showed no apparent increase in level of aggregation over time, and no precipitation or cloudiness was observed after 5 times of repeated freezing and thawing.

Example 8 In Vivo Anti-Tumor Efficacy of Mouse C1E1 Antibody

In vivo anti-tumor activity of mouse C1E1 antibody was evaluated in NCG mice. Briefly, NCG mice were subcutaneously injected with $4\times10^6$ human melanoma A375 cells mixed with $5\times10^5$ tumor reactivated PBMCs at the right axilla on Day 1. Tumor volumes were measured twice a week for three weeks using electronic caliper and calculated as (length×width$^2$)/2. Twenty-four tumor-bearing mice were selected and randomized into four groups on Day 14. The animals were intraperitoneally administered with vehicle (5% Glucose Solution), mouse C1E1, mouse C1E1 Fab, and Nivolumab, respectively at a dose of 3 mg/kg, on Day 14, 21 and 28. The mouse antibody C1E1 contained mouse heavy chain variable region and human IgG1 constant region as well as mouse light chain variable region and human Ck1 constant region having the sequences set forth in SEQ ID NOs: 67, 97, 80 and 98, respectively, while mouse C1E1 Fab contained mouse heavy chain variable domain and human IgG1 $CH_1$ constant domain as well as light chain variable domain and human Ck1 constant domain having the sequences set forth in SEQ ID NOs: 67, 99, 80 and 98, respectively.

The mice were euthanized on Day 35, and tumors were collected and weighed. Tumor growth inhibition (% TGI=(1-mean tumor volume in each treatment group/mean tumor volume in control group)×100%) was calculated.

All treatments were well tolerated by the tumor-bearing animals. As can be seen in Table 10, both mouse C1E1 treatment at 3 mg/kg and mouse C1E1 Fab treatment at 3 mg/kg had significantly better efficacy than Nivolumab at 3 mg/kg on humane melanoma A375 xenograft model.

TABLE 10

Anti-tumor Efficacy of Mouse CIE1 Antibody in the Human melanoma cell A375 Xenograft Model

| Group No. | Drug | Dose | Tumor Volume [a] ($mm^3$) | % TGI | Tumor weight (g) |
|---|---|---|---|---|---|
| 1 | Vehicle | n/a | 509.22 ± 132.69 | — | 0.61 ± 0.20 |
| 2 | Mouse C1E1 | 3 mg/kg | 116 ± 40.33* | 77.22% | 0.13 ± 0.06 |
| 3 | Mouse C1E1 Fab | 3 mg/kg | 91.38 ± 33.17* | 82.05% | 0.11 ± 0.04 |
| 4 | OPDIVO ® | 3 mg/kg | 276.47 ± 124.61 | 45.71% | 0.28 ± 0.12 |

[a] Compared with vehicle control group by student's t test, *P < 0.05.

Example 9 In Vivo Anti-Tumor Efficacy of Herpes Virus T3011 Inserted with Mouse C1E1-Encoding Sequences The anti-tumor efficacy of Herpes Virus T3011 inserted with the mouse C1E1 antibody-encoding sequences was evaluated on B16F10-hPD-L1 melanoma Xenograft Model.

Herpes Virus T3011 is genetically modified Herpes Simplex Virus Type 1 (HSV-1) by removing Inverted Repeat Region and replaced by human IL-12 gene (see, e.g., PCT/CN2016/080025), in addition to insertion of C1E1 Fab fragment sequence into the genomic region between UL3-UL4. C1E1 Fab sequence contains mouse heavy chain variable domain and human IgG1 $CH_1$ constant domain as well as mouse light chain variable domain and human Ckappal constant domain having the sequences set forth in SEQ ID NOs: 67, 99, 80 and 98, respectively.

Briefly, female B-hPD-1 humanized mice were subcutaneously injected with $1\times10^5$ B16F10-hPD-L1 melanoma cells at the right anterior flank. When tumor volumes reached approximately 90 $mm^3$, the mice were randomized into five groups, with 8 mice in each group. These mice were intratumorally administrated with vehicle (5% Glucose Solution), T3011 ($5\times10^6$ PFU/mouse), T3011 ($1\times10^7$ PFU/mouse), T3011 ($3\times10^7$ PFU/mouse) and NV1020 ($3\times10^7$ PFU/mouse, a recombinant oncolytic HSV-based virus, being developed by MediGene (formerly NeuroVir) for the potential cancer treatment, see e.g, Phase I/II study of oncolytic herpes simplex virus NV1020 in patients with extensively pretreated refractory colorectal cancer metastatic to the liver. *Hum Gene Ther.* 2010 September;21(9): 1119-28), respectively. Tumor volumes were measured twice a week.

Twelve days after drug administration, the mice were euthanized and tumors were collected, weighted and photographed. Relative tumor volume ($RTV=TVn/TV_0$, where TVn referred to the tumor volume at day n and $TV_0$ referred to the tumor volume at day 0), tumor growth inhibition rate (TGI %=1-mean tumor volume in each treatment group/mean tumor volume in control group)×100%) and tumor weight inhibition rate ($IR_{TW}$=(1-mean tumor weight in each treatment group/mean tumor weight in control group)×100%) were calculated.

As showed in Table 11 below, T3011 inserted with the mouse C1E1 antibody-encoding sequences provided evident anti-tumor activity in a dose-dependent manner. T3011 administration showed better anti-tumor efficacy than NV1020 administration at $3\times10^7$ PFU/mouse dose level.

TABLE 11

Anti-tumor Efficacy of Herpes Virus T3011 Inserted with Mouse C1E1-encoding Sequences against B16F10-hPD-L1 melanoma Xenograft Model

| Group No. | Drug | Dose | Tumor Volume[a] ($mm^3$) | TGI (%) | $IR_{TW}$ |
|---|---|---|---|---|---|
| 1 | Vehicle | n/a | 3396 ± 836 | — | — |
| 2 | T3011 | $5\times10^6$ PFU/mouse | 1724 ± 471* | 50.6% | 18.9% |
| 3 | T3011 | $1\times10^7$ PFU/mouse | 1365 ± 361* | 61.4% | 28.4% |
| 4 | T3011 | $3\times10^7$ PFU/mouse | 458 ± 128** | 88.9% | 73.6% |
| 5 | NV1020 | $3\times10^7$ PFU/mouse | 1277 ± 423* | 64.1% | 41.2% |

[a]Compared with vehicle control group by student's t test, *P<0.05 and **P<0.01.

Example 12 In Vivo Anti-Tumor Efficacy of Humanized C1E1 Antibody

The effect of humanized C1E1 antibodies on tumor growth was evaluated on MC38 xenograft model. Briefly, female B-hPD-1 mice were subcutaneously injected with $5\times10^5$ cells at the right hind flank. When tumor volumes reached about 100-150 $mm^3$, mice were randomly divided into 7 groups, 8 mice/group. The animals were intraperitoneally administered with vehicle (PBS), huC1E1-V10 and OPDIVO®, respectively, at a dose of 1 mg/kg, 3 mg/kg or 10 mg/kg, twice a week, for three weeks. The humanized antibody huC1E1-V10 contained heavy chain variable region and constant region as well as light chain variable region and constant region having the sequences set forth in SEQ ID NOs: 69, 97, 86 and 98, respectively. Tumor volumes were measured during the study.

Twenty-three days after treatment initiation, mice were euthanized and tumors were collected, weighted and photographed. Tumor volume growth inhibition rate ($TGI_{TV}$) were calculated and showed in Table 12.

As showed in Table 12 below, all treatments were tolerated well by the tumor-bearing animals. HuC1E1-V10 treatments showed anti-tumor activity in MC38 xenograft model in a dose-dependent manner, which was comparable to OPDIVO®.

TABLE 12

Anti-tumor Efficacy of huC1E1-V10 in MC38 xenograft model

| Group No. | Drug | Treatment Group | Tumor Volume [a] ($mm^3$) | $TGI_{TV}$ (%) |
|---|---|---|---|---|
| 1 | Vehicle | n/a | 3438 ± 571 | — |
| 2 | huC1E1-V10 | 1 mg/kg | 2357 ± 410 | 32.6 |
| 3 | huC1E1-V10 | 3 mg/kg | 1335 ± 241* | 63.4 |
| 4 | huC1E1-V10 | 10 mg/kg | 1189 ± 250* | 67.8 |
| 5 | OPDIVO ® | 1 mg/kg | 1255 ± 139 | 65.9 |

TABLE 12-continued

Anti-tumor Efficacy of huC1E1-V10 in MC38 xenograft model

| Group No. | Drug | Treatment Group | Tumor Volume [a] ($mm^3$) | $TGI_{TV}$ (%) |
|---|---|---|---|---|
| 6 | OPDIVO ® | 3 mg/kg | 1444 ± 190** | 60.2 |
| 7 | OPDIVO ® | 10 mg/kg | 703 ± 151* | 82.5 |

[a] Compared with vehicle control group by student's t test, *P<0.05 and **P<0.01.

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/Sequence/SEQ ID NO. |
|---|
| VH-CDR1 for C1EL huC1E1-V1 - huC1E1-V7 and huC1E1-V10<br>GFTFSSYL (SEQ ID NO: 1) |
| VH-CDR2 for C1EL huC1E1-V1 - huC1E1-V7 and huC1E1-V10<br>ISGGGGDT (SEQ ID NO: 2) |
| VH-CDR3 for C1EL huC1E1-V1 - huC1E1-V7 and huC1E1-V10<br>VRFGGAGYYWYFD (SEQ ID NO: 3) |
| VH-CDR1 for D1F2<br>GFTFSSYT (SEQ ID NO: 4) |
| VH-CDR2 for D1F2<br>ISGGGSNI (SEQ ID NO: 5) |
| VH-CDR3 for D1F2<br>VLNYAYAMDYWGQ (SEQ ID NO: 6) |
| VH-CDR1 for C1F5<br>GFAFSSYD (SEQ ID NO: 7) |
| VH-CDR2 for C1F5<br>ITGGGSSS (SEQ ID NO: 8) |
| VH-CDR3 for C1F5<br>ASPYLSYFDYWGQ (SEQ ID NO: 9) |
| VH-CDR1 for D1A1<br>GFTFSNYA (SEQ ID NO: 10) |
| VH-CDR2 for D1A1<br>ISGGGGNI (SEQ ID NO: 11) |
| VH-CDR3 for D1A1<br>ASPYANYVWYLDV (SEQ ID NO: 12) |
| VH-CDR1 for D1F1<br>GFTFSSNT (SEQ ID NO: 13) |
| VH-CDR2 for D1F1<br>ISGGGVNT (SEQ ID NO: 14) |
| VH-CDR3 for D1F1<br>ARHGNYNYYGMDY (SEQ ID NO: 15) |
| VH-CDR1 for C1E2<br>GYTFTNYW (SEQ ID NO: 16) |
| VH-CDR2 for C1E2<br>IYPGGGYT (SEQ ID NO: 17) |
| VH-CDR3 for C1E2<br>ARGYGTNYWYFDV (SEQ ID NO: 18) |

-continued

| Description/Sequence/SEQ ID NO. |
|---|
| VH-CDR1 for C1A1<br>GFSLSTSGMG (SEQ ID NO: 19) |
| VH-CDR2 for C1A1<br>IWWDDDK (SEQ ID NO: 20) |
| VH-CDR3 for C1A1<br>ARTGGFITTGYWY (SEQ ID NO: 21) |
| VH-CDR1 for C1F4<br>GYKFTDYA (SEQ ID NO: 22) |
| VH-CDR2 for C1F4<br>ISTYSGDV (SEQ ID NO: 23) |
| VH-CDR3 for C1F4<br>SRLGITAGFAYWG (SEQ ID NO: 24) |
| VH-CDR1 for D2C2<br>GFTFSSNT (SEQ ID NO: 25) |
| VH-CDR2 for D2C2<br>ISGGGVDT (SEQ ID NO: 26) |
| VH-CDR3 for D2C2<br>ARHGNYNYYGMDY (SEQ ID NO: 27) |
| VH-CDR1 for 2G2<br>GFTFSYYG (SEQ ID NO: 28) |
| VH-CDR2 for 2G2<br>ISSGSSFT (SEQ ID NO: 29) |
| VH-CDR3 for 2G2<br>TRREGIYDASWDY (SEQ ID NO: 30) |
| VH-CDR1 for C1C5<br>GYTFTNYG (SEQ ID NO: 31) |
| VH-CDR2 for C1C5<br>INTYSGEP (SEQ ID NO: 32) |
| VH-CDR3 for C1C5<br>VRQGDFDYEDAMD (SEQ ID NO: 33) |
| VL-CDR1 for CIEL huC1E1-V1 - huC1E1-V7 and huC1E1-V10<br>RASKSVDDSGISFMH (SEQ ID NO: 34) |
| VL-CDR2 for CIEL huC1E1-V1 - huC1E1-V7 and huC1E1-V10<br>AASNQGS (SEQ ID NO: 35) |
| VL-CDR3 for CIEL huC1E1-V1 - huC1E1-V7 and huC1E1-V10<br>HQTKEVPWT (SEQ ID NO: 36) |
| VL-CDR1 for D1F2<br>RASQDISNFLN (SEQ ID NO: 37) |
| VL-CDR2 for D1F2<br>YTSRLQS (SEQ ID NO: 38) |
| VL-CDR3 for D1F2<br>QQGSSLPWT (SEQ ID NO: 39) |
| VL-CDR1 for C1F5<br>RASQSISNNLH (SEQ ID NO: 40) |
| VL-CDR2 for C1F5<br>GSQSMS (SEQ ID NO: 41) |
| VL-CDR3 for C1F5<br>QQSNSWPLT (SEQ ID NO: 42) |
| VL-CDR1 for D 1A1<br>RASQDISNYLN (SEQ ID NO: 43) |

-continued

| Description/Sequence/SEQ ID NO. |
| --- |
| VL-CDR2 for D 1A1<br>YTSRLHS (SEQ ID NO: 44) |
| VL-CDR3 for D 1A1<br>QQSNALPWT (SEQ ID NO: 45) |
| VL-CDR1 for D1F1<br>RASESVDNSGISFMN (SEQ ID NO: 46) |
| VL-CDR2 for D1F1<br>TASNQGS (SEQ ID NO: 47) |
| VL-CDR3 for D1F1<br>QQSYEVPWT (SEQ ID NO: 48) |
| VL-CDR1 for C1E2<br>KASQSVSNDVA (SEQ ID NO: 49) |
| VL-CDR2 for C1E2<br>YAFFIRYT (SEQ ID NO: 50) |
| VL-CDR3 for C1E2<br>QQDYSSPYT(SEQ ID NO: 51) |
| VL-CDR1 for C1A1<br>RASQDISNYLI (SEQ ID NO: 52) |
| VL-CDR2 for C1A1<br>YTSRLHS (SEQ ID NO: 53) |
| VL-CDR3 for C1A1<br>QQHKTLPWT (SEQ ID NO: 54) |
| VL-CDR1 for C1F4<br>KASQNVRTAVA (SEQ ID NO: 55) |
| VL-CDR2 for C1F4<br>LASNRHT (SEQ ID NO: 56) |
| VL-CDR3 for C1F4<br>LQHWNYPYT (SEQ ID NO: 57) |
| VL-CDR1 for D2C2<br>RASESVDNSGISFMN (SEQ ID NO: 58) |
| VL-CDR2 for D2C2<br>IASNHGS (SEQ ID NO: 59) |
| VL-CDR3 for D2C2<br>QQSYEVPWT (SEQ ID NO: 60) |
| VL-CDR1 for 2G2<br>RSSQSIIRSNGNTYLE (SEQ ID NO: 61) |
| VL-CDR2 for 2G2<br>KVSNRFS (SEQ ID NO: 62) |
| VL-CDR3 for 2G2<br>FQGSHVPWT (SEQ ID NO: 63) |
| VL-CDR1 for C1C5<br>RSSQSIVHSNGHIYLE (SEQ ID NO: 64) |
| VL-CDR2 for C1C5<br>KVSKRFS (SEQ ID NO: 65) |
| VL-CDR3 for C1C5<br>FQGSHGT (SEQ ID NO: 66) |
| VH for C1E1<br>EVMLVESGGGLVKPGGSLKLSCAASGFTFSSYLMSWVRQTPEKRLEWVATISGGGGDTYFPD<br>SVKGRFTISRDNVKNNLYLQMSSLRSEDTALYYCVRFGGAGYYWYFDVWGAGTTVTVSS<br>(SEQ ID NO: 67)<br>GAAGTGATGCTGGTGGAGTCTGGGGGAGGGTTAGTGAAGCCTGGAGGGTCCCTGAAACTCTC<br>CTGTGCAGCCTCTGGATTCACGTTCAGTAGTTATCTTATGTCTTGGGTTCGCCAGACTCCGG<br>AGAAGAGGCTGGAGTGGGTCGCAACCATTAGTGGTGGTGGTGGTGACACCTACTTTCCAGAC |

| Description/Sequence/SEQ ID NO. |
| --- |

AGTGTGAAGGGTCGATTCACCATCTCCAGAGACAATGTCAAGAACAACCTGTACCTGCAAAT
GAGCAGTCTTAGGTCTGAGGACACGGCCTTGTATTACTGTGTAAGATTTGGGGGCGCTGGTT
ACTACTGGTATTTCGATGTCTGGGGCGCAGGGACCACGGTCACCGTCTCCTCA (SEQ ID
NO: 102)

VH for huC1E1-V1, huC1E1-V3-huC1E1-V7
EVQLVESGGGVVQPGRSLRLSCAASGFTFSSYLMSWVRQAPGKGLEWVATISGGGGDTYFPD
SVKGRFTISRDNSKNTLYLQMNSLRAEDTAVYYCVRFGGAGYYWYFDVWGAGTLVTVSS
(SEQ ID NO: 68)

VH for huC1E1-V2 and huC1E1-V10
EVQLVESGGGVVQPGRSLRLSCAASGFTFSSYLMSWVRQAPGKGLEWVATISGGGGDTYFPD
SVKGRFTISRDNSKNTLYLQMNSLRAEDTAVYYCVRFGGAGYYWYFDVWGQGTLVTVSS
(SEQ ID NO: 69)
GAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATCTTATGTCCTGGGTCCGCCAGGCTCCAG
GCAAGGGGCTAGAGTGGGTGGCAACTATATCAGGTGGTGGAGGTGACACATACTTCCCAGAC
TCCGTGAAGGGCCGATTCACCATCTCCAGAGACAATTCCAAGAACACGCTGTATCTGCAAAT
GAACAGCCTGAGAGCTGAGGACACGGCTGTGTATTACTGTGTGAGATTCGGTGGTGCTGGTT
ACTACTGGTACTTTGACGTCTGGGGCCAAGGAACCCTGGTCACCGTCTCGAGT (SEQ ID
NO: 103)

VH for D1F2
EVMLVESGGGLVKPGGSLKLSCAASGFTFSSYTMSWVRQTPEKRLEWVATISGGGSNIYYPD
SVEGRFTVSRDNARNTLYLHMSSLRSEDTALYYCVLNYAYAMDYWGQGTSVTVSS (SEQ
ID NO: 70)
GAAGTGATGCTGGTGGAGTCTGGGGGAGGCTTAGTGAAGCCTGGAGGGTCCCTGAAACTCTC
CTGTGCAGCCTCTGGATTCACTTTCAGTAGCTATACCATGTCTTGGGTTCGCCAGACTCCGG
AGAAGAGGCTGGAGTGGGTCGCAACCATTAGTGGTGGTGGTAGTAACATCTACTATCCAGAC
AGTGTGGAGGGTCGATTCACCGTCTCCAGAGACAATGCCAGGAACACCCTGTACCTGCATAT
GAGCAGTCTGAGGTCTGAGGACACGGCCTTATATTACTGTGTCCTTAACTACGCCTATGCTA
TGGACTACTGGGGTCAAGGAACCCTCAGTCACCGTCTCCTCA (SEQ ID NO: 104)

VH for C1F5
EVQLVESGGGLVKPGGSLKLSCAASGFAFSSYDMSWVRQTPEKRLEWVAYITGGGSSSFYPD
TVKGRFTISRDNSKNTLYLQMTSLRSEDTAMYYCASPYLSYFDYWGQGTTLTVSS (SEQ
ID NO: 71)
GAAGTGCAGCTGGTGGAGTCTGGGGGAGGCTTAGTGAAGCCTGGAGGGTCCCTGAAACTCTC
CTGTGCAGCCTCTGGATTCGCTTTCAGTAGCTATGACATGTCTTGGGTTCGCCAGACTCCGG
AGAAGAGGCTGGAGTGGGTCGCATACATTACTGGTGGTGGTAGTAGTTCCTTCTATCCAGAC
ACTGTGAAGGGCCGATTCACCATCTCCAGAGACAATTCCAAGAACACCCTGTATTTGCAAAT
GACCAGTCTGAGGTCTGAGGACACAGCCATGTATTACTGTGCAAGCCCCTACTTATCCTACT
TTGACTACTGGGGCCAAGGCACCACTCTCACAGTCTCCTCA (SEQ ID NO: 105)

VH for D1A1
EVMLVESGGGLVKPGGSLKLSCAASGFTFSNYAMSWVRQTPEKRLEWVATISGGGGNIYYPD
SVKGRFTISRDNARNTLYLQMSSLRSEDTALYYCASPYANYVWYLDVWGAGTTVTVSS
(SEQ ID NO: 72)
GAAGTGATGCTGGTGGAGTCTGGGGGAGGCTTAGTGAAGCCTGGAGGGTCCCTGAAACTCTC
CTGTGCAGCCTCTGGATTCACTTTCAGTAACTATGCCATGTCTTGGGTTCGCCAGACTCCGG
AGAAGAGGCTGGAGTGGGTCGCAACCATTAGTGGTGGTGGTAATACATCTACTATCCAGAC
AGTGTGAAGGGTCGATTCACCATCTCCAGAGACAATGCCAGGAACACCCTGTACCTGCAAAT
GAGCAGTCTGAGGTCTGAGGACACGGCCTTGTATTATTGTGCAAGCCCGTATGCTAACTACG
TATGGTACCTCGATGTCTGGGGCGCAGGGACCACGGTCACCGTCTCCTCA (SEQ ID NO:
106)

VH for D1F1
EVMLVESGGGLVKPGGSLKLSCAASGFTFSSNTMSWVRQTPEKRLEWVAAISGGGVNTYYPD
SVKGRFTISRDNARNTLYLQMSSLRSEDTALYYCARHGNYNYYGMDYWGQGTSVTVSS
(SEQ ID NO: 73)
GAAGTGATGCTGGTGGAGTCTGGGGGAGGCTTAGTGAAGCCTGGAGGGTCCCTGAAACTCTC
CTGTGCAGCCTCTGGATTCACTTTCAGTAGCAATACCATGTCTTGGGTTCGCCAGACTCCGG
AGAAGAGGCTGGAGTGGGTCGCAGCCATTAGTGGTGGTGGTGTTAACACCTACTATCCAGAC
AGTGTGAAGGGTCGATTCACCATCTCCAGAGACAATGCCAGGAACACCCTGTACCTGCAAAT
GAGCAGTCTGAGGTCTGAGGACACGGCCCTGTATTACTGTGCAAGACATGGTAACTACAATT
ACTATGGTATGGACTACTGGGGTCAAGGAACCTCAGTCACCGTCTCCTCA (SEQ ID NO:
107)

VH for C1E2
QVQLQQSGAELVRPGTSVKISCKAS GYTFTNYWLGWVKQRPGHGLEWIGDIYPGGGYTNYN
ENFKGKATLTADTSSSTAYMQLSSLTSEDSAVFFCARGYGTNYWYFDVWGAGTTVTVSS
(SEQ ID NO: 74)
CAGGTCCAGTTGCAGCAGTCTGGAGCTGAGCTGGTAAGGCCTGGGACTTCAGTGAAGATATC
CTGCAAGGCTTCTGGCTACACCTTCACTAACTACTGGCTAGGTTGGGTAAAACAGAGGCCTG
GACATGGACTTGAGTGGATTGGAGATATTTACCCTGGAGGTGGTTATACTAACTACAATGAG
AACTTCAAGGGCAAGGCCACACTGACTGCAGACACATCCTCCAGCACTGCCTACATGCAGCT -continued

| Description/Sequence/SEQ ID NO. |
|---|
| CAGTAGCCTGACATCTGAGGACTCTGCTGTCTTTTTCTGTGCAAGAGGCTACGGTACTAATT ACTGGTACTTCGATGTCTGGGGCGCAGGGACCACGGTCACCGTCTCCTCA (SEQ ID NO: 108) |
| VH for C1A1<br>QVTLKESGPGILKPSQTLSLTCSFSGFSLSTSGMGVGWIRQPSGKGLEWLAHIWWDDDKFYN PSLKSQLTISKDTSRNQVFLKITSVDTADTATYYCARTGGFITTGYWYFDVWGAGTTVTVSS (SEQ ID NO: 75)<br>CAAGTTACTCTAAAAGAGTCTGGCCCTGGGATATTGAAGCCCTCACAGACCCTCAGTCTGAC TTGTTCTTTCTCTGGGTTTTCACTGAGCACTTCTGGTATGGGTGTAGGCTGGATTCGTCAGC CTTCAGGGAAGGGTCTGGAGTGGCTGGCACACATTTGGTGGGATGATGATAAGTTCTATAAC CCATCCCTGAAGAGCCAGCTCACAATCTCCAAGGATACCTCCAGAAACCAGGTTTTCCTCAA GATCACCAGTGTGGACACTGCAGATACTGCCACTTACTACTGTGCTCGAACCGGGGGGTTTA TTACTACGGGCTACTGGTACTTCGATGTCTGGGGCGCAGGGACCACGGTCACCGTCTCCTCA (SEQ ID NO: 109) |
| VH for C1F4<br>QVQLQQSGAELVRPGVSVKISCKGSGYKFTDYAMHWVRQSHAKSLEWIGIISTYSGDVSFNQ NFKGKATMTVDKSSSTAYMELARLTSEDSAIYYCSRLGITAGFAYWGQGTLVTVSA (SEQ ID NO: 76)<br>CAGGTCCAGCTGCAACAGTCTGGGGCTGAGCTGGTGAGGCCTGGGGTCTCAGTGAAGATTTC CTGCAAGGGTTCTGGCTACAAATTCACTGATTATGCTATGCACTGGGTGAGGCAGAGTCATG CAAAGAGTCTAGAGTGGATTGGAATTATTAGTACTTACTCTGGTGACGTTAGTTTCAACCAG AACTTCAAGGGCAAGGCCACAATGACTGTAGACAAATCCTCCAGCACAGCCTATATGGAACT TGCCAGACTGACATCTGAGGATTCTGCCATCTATTACTGTTCAAGACTGGGGATTACGGCGG GGTTTGCTTACTGGGGCCAAGGGACTCTGGTCACTGTCTCTGCA (SEQ ID NO: 110) |
| VH for D2C2<br>EVMLVESGGGLVKPGGSLKLSCAASGFTFSSNTMSWVRQTPEKRLEWVAAISGGGVDTYYPD SVKGRFTISRDNARNTLYLQMSSLRSEDTALYYCARHGNYNYYGMDYWGQGTSVTVSS (SEQ ID NO: 77)<br>GAAGTGATGCTGGTGGAGTCTGGGGGAGGCTTAGTGAAGCCTGGAGGGTCCCTGAAACTCTC CTGTGCAGCCTCTGGATTCACTTTCAGTAGCAATACCATGTCTTGGGTTCGCCAGACTCCGG AGAAGAGGCTGGAGTGGGTCGCAGCCATTAGTGGTGGTGGTGTTGACACCTACTATCCAGAC AGTGTGAAGGGTCGATTCACCATCTCCAGAGACAATGCCAGGAACACCCTGTACCTGCAAAT GAGCAGTCTGAGGTCTGAGGACACGGCCCTGTATTACTGTGCAAGACATGGTAACTACAATT ACTATGGTATGGACTACTGGGGTCAAGGAACCTCAGTCACCGTCTCCTCA (SEQ ID NO: 111) |
| VH for 2G2<br>EVQLVESGGDLVKPGGSLKLSCTASGFTFSYYGMSWVRQTPDKRLEWVATISSGSSFTYSPD SVKGRFTISRDNAKNTLYLQMNSLKSEDTAIYYCTRREGIYDASWDYSMDYWGQGTSVTVSS (SEQ ID NO: 78)<br>GAGGTGCAACTGGTGGAGTCTGGGGGAGACTTAGTGAAGCCTGGAGGGTCCCTGAAACTCTC CTGTACAGCCTCTGGATTCACTTTCAGTTACTATGGCATGTCTTGGGTTCGCCAGACTCCAG ACAAGAGGCTGGAATGGGTCGCAACCATTAGTAGTGGTAGTAGTTTCACCTACTCTCCAGAC AGTGTGAAGGGGCGATTCACCATCTCCAGAGACAATGCCAAGAACACCCTGTACCTACAAAT GAACAGTCTGAAGTCTGAGGACACAGCCATTTATTACTGTACAAGACGAGAGGGGATCTATG ATGCTTCCTGGGATTATTCTATGGACTACTGGGGTCAAGGAACCTCAGTCACCGTCTCCTCA (SEQ ID NO: 112) |
| VH for C1C5<br>QIQLVQSGPELKKPGETVKISCKASGYTFTNYGINWVKQAPGKGLKWMGWINTYSGEPTYSD DFKGRFAFSLETSASTAYLQINNLKNEDTSTYFCVRQGDFDYEDAMDYWGQGTSVTVSS (SEQ ID NO: 79)<br>CAGATCCAGTTGGTGCAGTCAGGACCTGAGCTGAAGAAGCCTGGAGAGACAGTCAAGATCTC CTGCAAGGCTTCTGGGTATACCTTCACAAACTATGGAATAAACTGGGTGAAGCAGGCTCCAG GAAAGGGTTTAAAGTGGATGGGCTGGATAAACACCTATAGTGGAGAGCCAACATATTCTGAT GACTTCAAGGGACGCTTTGCCTTCTCTTTGGAAACCTCTGCCAGCACTGCCTATTTGCAGAT CAACAACCTCAAAAATGAGGACACGTCTACATATTTCTGTGTAAGACAGGGGGACTTTGATT ACGAGGATGCTATGGACTACTGGGGTCAAGGAACCTCAGTCACCGTCTCCTCA (SEQ ID NO: 113) |
| VL for C1E1<br>DIVLTQSPASLAVSLGQRATISCRASKSVDDSGISFMHWFQQKPGQPPKLLIYAASNQGSGV PARFRGSGSGTDFSLNIIIPMEEDDTAMYFCHQTKEVPWTFGGGTKLEIK (SEQ ID NO: 80)<br>GACATTGTGCTGACCCAATCTCCAGCTTCTTTGGCTGTGTCTCTAGGGCAGAGGGCCACCAT CTCCTGCAGAGCCAGCAAAAGTGTTGATGATTCTGGCATTAGTTTTATGCACTGGTTCCAAC AGAAACCAGGACAGCCACCCAAACTCCTCATCTATGCTGCATCCAACCAAGGATCCGGGGTC CCTGCCAGGTTTCGTGGCAGTGGGTCTGGGACAGACTTCAGCCTCAACATCCATCCTATGGA GGAGGATGATACTGCAATGTATTTCTGTCACCAAACTAAGGAGGTTCCGTGGACGTTCGGTG GAG GCACCAAGCTGGAAATCAAA (SEQ ID NO: 114) |
| VL for huC1E1-V1 and huC1E1-V2<br>EIVLTQSPATLSLSPGERATLSCRASKSVDDSGISFMHWFQQKPGQPPRLLIYAASNQGSGV PARFSGSGSGTDFTLTISSLEPEDFAVYFCHQTKEVPWTFGQGTKVEIK (SEQ ID NO: 81) |

-continued

| Description/Sequence/SEQ ID NO. |
|---|

VL for huC1E1-V3
EIVLTQSPATLSLSPGERATLSCRASKSVDDSGISFMHWYQQKPGQPPRLLIYAASNQGSGV
PARFSGSGSGTDFTLTISSLEPEDFAVYFCHQTKEVPWTFGQGTKVEIK (SEQ ID NO: 82)

VL for huC1E1-V4
EIVLTQSPATLSLSPGERATLSCRASKSVDDSGISFMHWFQQKPGQAPRLLIYAASNQGSGV
PARFSGSGSGTDFTLTISSLEPEDFAVYFCHQTKEVPWTFGQGTKVEIK (SEQ ID NO: 83)

VL for huC1E1-V5
EIVLTQSPATLSLSPGERATLSCRASKSVDDSGISFMHWFQQKPGQPPRLLIYAASNQGSGI
PARFSGSGSGTDFTLTISSLEPEDFAVYFCHQTKEVPWTFGQGTKVEIK (SEQ ID NO: 84)

VL for huC1E1-V6
EIVLTQSPATLSLSPGERATLSCRASKSVDDSGISFMHWFQQKPGQPPRLLIYAASNQGSGV
PARFSGSGSGTDFTLTISSLEPEDFAVYYCHQTKEVPWTFGQGTKVEIK (SEQ ID NO: 85)

VL for huC1E1-V7 and huC1E1-V10
EIVLTQSPATLSLSPGERATLSCRASKSVDDSGISFMHWYQQKPGQAPRLLIYAASNQGSGI
PARFSGSGSGTDFTLTISSLEPEDFAVYYCHQTKEVPWTFGQGTKVEIK (SEQ ID NO: 86)
GAAATTGTGTTGACACAGTCTCCAGCCACCCTGTCTTTGTCTCCAGGGGAAAGAGCCACCCT
CTCCTGCAGGGCCAGTAAGTCTGTTGACGACAGTGGTATCAGCTTCATGCACTGGTATCAAC
AGAAACCTGGCCAGGCTCCCAGGCTCCTCATCTATGCTGCATCCAACCAGGGCTCTGGCATC
CCAGCCAGGTTCAGTGGCAGTGGGTCTGGGACAGACTTCACTCTCACCATCAGCAGCCTAGA
GCCTGAAGATTTTGCAGTTTATTACTGTCATCAGACTAAGGAGGTGCCTTGGACGTTCGGCC
AAGGGACCAAGGTGGAGATCAAA (SEQ ID NO: 115)

VL for D1F2
DIQMTQTTSSLSASLGDRVTISCRASQDISNFLNWYQQKPDGTVKLLIYYTSRLQSGVPSRF
SGTGSGTDYSLTISNLEQEDLATYFCQQGSSLPWTFGGGTKLEIK (SEQ ID NO: 87)
GATATCCAGATGACACAGACTACATCCTCCCTGTCTGCCTCTCTGGGAGACAGAGTCACCAT
CAGTTGCAGGGCCAGTCAGGACATTAGCAATTTTTTAAACTGGTATCAGCAGAAACCAGATG
GAACTGTTAAACTCCTGATCTACTACACATCAAGATTACAGTCAGGAGTCCCATCAAGGTTC
AGTGGCACTGGGTCTGGGACAGATTATTCTCTCACCATTAGCAACCTGGAACAAGAAGATCT
TGCCACTTACTTTTGCCAACAGGGTAGTTCGCTTCCGTGGACGTTCGGTGGAGGCACCAAGC
TGGAAATCAAA (SEQ ID NO: 116)

VL for C1F5
DIVLTQSPATLSVTPGDSVSLSCRASQSISNNLHWYQQKSHESPRLLIKYGSQSMSGIPSRF
SGSGSGTDFTLVINSVETEDFGMYFCQQSNSWPLTFGAGTKLELK (SEQ ID NO: 88)
GATATTGTGCTAACTCAGTCTCCAGCCACCCTGTCTGTGACTCCAGGAGATAGCGTCAGTCT
TTCCTGCAGGGCCAGCCAAAGTATTAGCAACAACCTACACTGGTATCAACAAAAATCACATG
AGTCTCCAAGGCTTCTCATCAAGTATGGTTCCCAGTCCATGTCTGGGATCCCCTCCAGGTTC
AGTGGCAGTGGATCAGGGACAGATTTCACTCTCGTTATCAACAGTGTGGAGACTGAAGATTT
TGGAATGTATTTCTGTCAACAGAGTAACAGCTGGCCTCTCACGTTCGGTGCTGGGACCAAGC
TGGAGCTGAAA (SEQ ID NO: 117)

VL for D1A1
DIQMTQTTSSLSASLGDRVTISCRASQDISNYLNWYQQKPDGTVKLLIYYTSRLHSGVPSRF
SGSGSGTDFSLTISNLEEEDIATYFCQQSNALPWTFGGGTKLEIK (SEQ ID NO: 89)
GATATCCAGATGACACAGACTACATCCTCCCTGTCTGCCTCTCTGGGAGACAGAGTCACCAT
CAGTTGCAGGGCAAGTCAGGACATTAGCAATTATTTAAACTGGTATCAGCAGAAACCAGATG
GAACTGTTAAACTCCTGATCTACTACACATCAAGATTACACTCAGGAGTCCCATCAAGGTTC
AGTGGCAGTGGGTCTGGAACAGATTTTTCTCTCACCATTAGCAACCTGGAAGAAGAAGATAT
TGCCACTTACTTTTGCCAACAGAGTAATGCGCTTCCGTGGACGTTCGGTGGAGGCACCAAAC
TGGAAATCAAA (SEQ ID NO: 118)

VL for D1F1
DIVLTQSPASLVVSLGQRATISCRASESVDNSGISFMNWFQQKPGQPPKWYTASNQGSGVPA
RFSGSGSGTDFSLNIFIPMEEDDSAMYFCQQSYEVPWTFGGGTKLEIK (SEQ ID NO: 90)
GACATTGTGCTGACCCAATCTCCAGCTTCTTTGGTTGTGTCTCTAGGGCAGAGGGCCACCAT
CTCCTGCAGAGCCAGCGAAAGTGTTGATAATTCTGGCATTAGTTTTATGAACTGGTTCCAAC
AGAAACCAGGACAGCCACCCAAACTCCTCATCTATACTGCATCCAACCAAGGATCCGGGGTC
CCTGCCAGGTTTAGTGGCAGTGGGTCTGGGACAGACTTCAGCCTCAACATCCATCCTATGGA
GGAGGATGATTCTGCAATGTATTTCTGTCAGCAAAGTTATGAGGTTCCTTGGACGTTCGGTG
GAGGCACCAAGCTGGAAATCAAA (SEQ ID NO: 119)

VL for C1E2
SIVMTQTPKFLLVSAGDRVTITCKASQSVSNDVAWYQQKPGQSPKLLIYYAFHRYTGVPDRF
TGSGYGTDFTFTISTVQAEDLAVYFCQQDYSSPYTFGGGTKLEIK (SEQ ID NO: 91)
AGTATTGTGATGACCCAGACTCCCAAATTCCTGCTTGTATCAGCAGGAGACAGGGTTACCAT -continued

| Description/Sequence/SEQ ID NO. |
| --- |
| AACCTGCAAGGCCAGTCAGAGTGTGAGTAATGATGTAGCTTGGTACCAACAGAAGCCAGGGC AGTCTCCTAAACTGCTGATATACTATGCATTTCATCGCTACACTGGAGTCCCTGATCGCTTC ACTGGCAGTGGATATGGGACGGATTTCACTTTCACCATCAGCACTGTGCAGGCTGAAGACCT GGCAGTTTATTTCTGTCAGCAGGATTATAGCTCTCCGTACACGTTCGGAGGGGGGACCAAGC TGGAAATAAAA (SEQ ID NO: 120) |
| VL for C1A1<br>DIQMTQTTSSLSASLGDRVTISCRASQDISNYLIWYQQKTDGTLKLLIYYTSRLHSGVPSRF SGSGSGTDYSLTISNLEQEDIATYFCQQHKTLPWTFGGGTKLEIK (SEQ ID NO: 92)<br>GATATCCAGATGACACAGACTACATCCTCCCTGTCTGCCTCTCTGGGAGACAGAGTCACCAT CAGTTGCAGGGCAAGTCAGGACATTAGCAATTATTTAATCTGGTATCAGCAGAAAACAGATG GAACTCTTAAACTCCTGATCTACTACACATCAAGATTACACTCAGGAGTCCCATCAAGGTTC AGTGGCAGTGGGTCTGGAACAGATTATTCTCTCACCATTAGCAACCTGGAGCAAGAAGATAT TGCCACTTACTTTTGCCAGCAGCATAAAACGCTTCCGTGGACGTTCGGTGGAGGCACCAAGC TGGAAATCAAA (SEQ ID NO: 121) |
| VL for C1F4<br>DIVMTQSQKFMSTSVGDRVTITCKASQNVRTAVAWYQQKPGQSPKALIYLASNRHTGVPDRF TGSGSGTDFTLTISNVQSKDLADYFCLQHWNYPYTFGGGTKLEIK (SEQ ID NO: 93)<br>GACATTGTGATGACCCAGTCTCAAAAATTCATGTCCACATCAGTAGGAGACAGGGTCACCAT CACCTGCAAGGCCAGTCAGAATGTTCGTACTGCTGTAGCCTGGTATCAACAGAAACCAGGGC AGTCTCCTAAAGCACTGATTTACTTGGCATCCAACCGGCACACTGGAGTCCCTGATCGCTTC ACAGGCAGTGGATCTGGGACAGATTTCACTCTCACCATTAGCAATGTGCAATCTAAAGACCT GGCAGATTATTTCTGTCTGCAACATTGGAATTATCCGTACACGTTCGGAGGGGGGACCAAGC TGGAAATAAAA (SEQ ID NO: 122) |
| VL for D2C2<br>DIVLTQSPASLAVSLGQRATISCRASESVDNSGISFMNWFQQKPGQSPKLLIYIASNHGSGV PARFSGSGSGTDFSLNIFIPMEEDDSAMYFCQQSYEVPWTFGGGTKLEIK (SEQ ID NO: 94)<br>GACATTGTGCTGACCCAATCTCCAGCTTCTTTGGCTGTGTCTCTAGGGCAGAGGGCCACCAT CTCCTGCAGAGCCAGCGAAAGTGTTGATAATTCTGGCATTAGTTTTATGAACTGGTTCCAAC AGAAACCAGGACAGTCACCCAAACTCCTCATCTATATTGCATCCAACCACGGATCCGGGGTC CCTGCCAGGTTTAGTGGCAGTGGGTCTGGGACAGACTTCAGCCTCAACATCCATCCTATGGA GGAGGATGATTCTGCAATGTATTTCTGTCAGCAAAGTTATGAGGTTCCTTGGACGTTCGGTG GAGGCACCAAGCTGGAAATCAAA (SEQ ID NO: 123) |
| VL for 2G2<br>DVLMTQTPLSLPVSLGDQASISCRSSQSIIRSNGNTYLEWYLQKPGQSPKWYKVSNRFSGVP DRFSGSGSGTDFTLKISRVEADDLGLYYCFQGSHVPWTFGGGTKLEIK (SEQ ID NO: 95)<br>GATGTTTTGATGACCCAAACTCCACTCTCCCTGCCTGTCAGTCTTGGAGATCAAGCCTCCAT CTCTTGCAGATCTAGTCAGAGCATTATACGTAGTAATGGAAACACCTATTTAGAATGGTACC TGCAGAAACCAGGCCAGTCTCCAAAGCTCCTGATCTACAAAGTTTCCAACCGATTTTCTGGG GTCCCAGACAGGTTCAGTGGCAGTGGATCAGGGACAGATTTCACACTCAAGATCAGCAGAGT GGAGGCTGACGATCTGGGACTTTATTACTGCTTTCAAGGTTCACATGTTCCGTGGACGTTCG GTGGAGGCACCAAGCTGGAAATCAAA (SEQ ID NO: 124) |
| VL for C1C5<br>DVLMTQSPLSLPVSLGDQASISCRSSQSIVHSNGHIYLEWYLQKPGQSPKWYKVSKRFSGVP DRFSGSGSGTDFTLKISRVEAEDLGVYYCFQGSHGTFGGGTKLEIK (SEQ ID NO: 96)<br>GATGTTTTGATGACCCAAAGTCCACTCTCCCTGCCTGTCAGTCTTGGAGATCAAGCCTCCAT CTCTTGCAGATCTAGTCAGAGTATTGTACATAGTAATGGACACATCTATTTAGAATGGTACC TGCAGAAACCAGGCCAGTCTCCAAAGCTCCTGATCTACAAAGTTTCCAAGCGATTTTCTGGG GTCCCAGACAGGTTCAGTGGCAGTGGATCAGGGACAGATTTCACACTCAAGATCAGCAGAGT GGAGGCTGAGGATCTGGGAGTTTATTACTGCTTTCAAGGTTCACATGGGACGTTCGGTGGAG GCACCAAGCTGGAAATCAAA (SEQ ID NO: 125) |
| human IgG1 heavy chain constant region<br>ASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQQGNVFSCSV MHEALHNHYTQKSLSLSPGK (SEQ ID NO: 97)<br>GCTAGCACCAAGGGCCCATCGGTCTTCCCCCTGGCACCCTCCTCCAAGAGCACCTCTGGGGG CACAGCGGCCCTGGGCTGCCTGGTCAAGGACTACTTCCCCGAACCGGTGACGGTGTCGTGGA ACTCAGGCGCCCTGACCAGCGGCGTGCACACCTTCCCGGCTGTCCTACAGTCCTCAGGACTC TACTCCCTCAGCAGCGTGGTGACCGTGCCCTCCAGCAGCTTGGGCACCCAGACCTACATCTG CAACGTGAATCACAAGCCCAGCAACACCAAGGTGGACAAGAAAGTTGAGCCCAAATCTTGTG ACAAAACTCACACATGCCCACCGTGCCCAGCACCTGAACTCCTGGGGGGACCGTCAGTCTTC CTCTTCCCCCCAAAACCCAAGGACACCCTCATGATCTCCCGGACCCCTGAGGTCACATGCGT GGTGGTGGACGTGAGCCACGAAGACCCTGAGGTCAAGTTCAACTGGTACGTGGACGGCGTGG AGGTGCATAATGCCAAGACAAAGCCGCGGGAGGAGCAGTACAACAGCACGTACCGTGTGGTC AGCGTCCTCACCGTCCTGCACCAGGACTGGCTGAATGGCAAGGAGTACAAGTGCAAGGTCTC CAACAAAGCCCTCCCAGCCCCCATCGAGAAAACCATCTCCAAAGCCAAAGGGCAGCCCCGAG AACCACAGGTGTACACCCTGCCCCCATCCCGGGAGGAGATGACCAAGAACCAGGTCAGCCTG |

-continued

| Description/Sequence/SEQ ID NO. |
|---|
| ACCTGCCTGGTCAAAGGCTTCTATCCCAGCGACATCGCCGTGGAGTGGGAGAGCAATGGGCA GCCGGAGAACAACTACAAGACCACGCCTCCCGTGCTGGACTCCGACGGCTCCTTCTTCCTCT ACAGCAAGCTCACCGTGGACAAGAGCAGGTGGCAGCAGGGGAACGTCTTCTCATGCTCCGTG ATGCATGAGGCTCTGCACAACCACTACACGCAGAAGAGCCTCTCCCTGTCTCCGGGTAAA (SEQ ID NO: 126) |
| human kappa light chain constant region RTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC (SEQ ID NO: 98) CGTACGGTGGCGGCGCCATCTGTCTTCATCTTCCCGCCATCTGATGAGCAGTTGAA ATCTGGAACTGCCTCTGTTGTGTGCCTGCTGAATAACTTCTATCCCAGAGAGGCCA AAGTACAGTGGAAGGTGGATAACGCCCTCCAATCGGGTAACTCCCAGGAGAGTGT CACAGAGCAGGACAGCAAGGACAGCACCTACAGCCTCAGCAGCACCCTGACGCT GAGCAAAGCAGACTACGAGAAACACAAAGTCTACGCCTGCGAAGTCACCCATCA GGGCCTGAGCTCGCCCGTCACAAAGAGCTTCAACAGGGGAGAGTGT (SEQ ID NO: 127) |
| human IgG1 heavy chain CH1 region ASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKV (SEQ ID NO:99) Gcctccaccaagggcccatcggtcttccccctggcaccctcctccaagagcacctctggggg cacagcggccctgggctgcctggtcaaggactacttccccgaaccggtgacggtgtcgtgga actcaggcgccctgaccagcggcgtgcacaccttcccggctgtcctacagtcctcaggactc tactccctcagca gcgtggtgaccgtgccctccagcagcttgggcacccagacctacatct gcaacgtgaatcacaagcccagcaacaccaaggtggacaagaaagtt (SEQ ID NO: 128) |
| human PD-1-Fc LDSPDRPWNPPTFSPALLVVTEGDNATFTCSFSNTSESFVLNWYRMSPSNQTDKLAAFPEDRS QPGQDCRFRVTQLPNGRDFHMSVVRARRNDSGTYLCGAISLAPKAQIKESLRAELRVTERRAE VPTAHPSPSPRPAGQFQEPKSCDKTHTCPPCPAPELLGGPSVFLFPPKPKDTLMISRTPEVTC VVVDVSHEDPEVKFNAVYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSLSL (SEQ ID NO: 100) |
| human PD-L1-Fc FTVTVPKDLYVVEYGSNMTIECKFPVEKQLDLAALIVYWEMEDKNIIQFVHGEEDLKVQHSS YRQRARLLKDQLSLGNAALQITDVKLQDAGVYRCMISYGGADYKRITVKVNAPYNKINQRIL VVDPVTSEHELTCQAEGYPKAEVIWTSSDHQVLSGKTTTTNSKREEKLFNVTSTLRINTTTN EIFYCTFRRLDPEENHTAELVIPELPLAHPPNERTEPKSCDKTHTCPPCPAPELLGGPSVFL FPPKPKDTLMISRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSREEMTKNQVSLT CLVKGFYPSDIAVEWESNGQPENNYKTTPPVLDSDGSFFLYSKLTVDKSRWQQGNVFSCSVM HEALHNHYTQKSLSLSPGK (SEQ ID NO: 101) |
| Heavy chain constant region for mouse antibodies AKTTPPSVYPLAPGSAAQTNSMVTLGCLVKGYFPEPVTVTWNSGSLSSGVHTFPAVL QSDLYTLSSSVTVPSSTWPSETVTCNVAHPASSTKVDKKIVPRDCGCKPCICTVPEVS SVFIFPPKPKDVLTITLTPKVTCVVVDISKDDPEVQFSWFVDDVEVHTAQTQPREEQF NSTFRSVSELPIMHQDWLNGKEFKCRVNSAAFPAPIEKTISKTKGRPKAPQVYTIPPPK EQMAKDKVSLTCMITDFFPEDITVEWQWNGQPAENYKNTQPIMDTDGSYFVYSKLN VQKSNWEAGNTFTCSVLHEGLHNHHTEKSLSHSPGK (SEQ ID NO: 129) |
| Light chain constant region for mouse antibodies RADAAPTVSIFPPSSEQLTSGGASVVCFLNNFYPKDINVKWKIDGSERQNGVLNSWT DQDSKDSTYSMSSTLTLTKDEYERHNSYTCEATHKTSTSPIVKSFNRGEC (SEQ ID NO: 130) |
| SEQ 1D NOs:1-101, 129 and 130: amino acid sequence; SEQ ID NOs: 102-128: nucleotide sequence |

We claim:

1. An isolated monoclonal antibody, or an antigen-binding portion thereof, binding to PD-1, comprising a heavy chain variable region comprising a heavy chain CDR1 region, a heavy chain CDR2 region and a heavy chain CDR3 region, and a light chain variable region comprising a light chain CDR1 region, a light chain CDR2 region and a light chain CDR3 region, wherein the heavy chain CDR1 region, the heavy chain CDR2 region, the heavy chain CDR3 region, the light chain CDR1 region, the light chain CDR2 region and the light chain CDR3 region comprise the amino acid sequences set forth in (i) SEQ ID NOs: 1, 2, 3, 34, 35, and 36, respectively;
(ii) SEQ ID NOs: 4, 5, 6, 37, 38, and 39, respectively;
(iii) SEQ ID NOs: 7, 8, 9, 40, 41, and 42, respectively;
(iv) SEQ ID NOs: 10, 11, 12, 43, 44, and 45, respectively;
(v) SEQ ID NOs: 13, 14, 15, 46, 47, and 48, respectively;
(vi) SEQ ID NOs: 16, 17, 18, 49, 50, and 51, respectively;
(vii) SEQ ID NOs: 19, 20, 21, 52, 53, and 54, respectively;
(viii) SEQ ID NOs: 22, 23, 24, 55, 56, and 57, respectively;
(ix) SEQ ID NOs: 25, 26, 27, 58, 59, and 60, respectively;
(x) SEQ ID NOs: 28, 29, 30, 61, 62, and 63, respectively; or
(xi) SEQ ID NOs: 31, 32, 33, 64, 65, and 66, respectively.

2. The isolated monoclonal antibody, or an antigen-binding portion thereof, of claim 1, wherein the heavy chain and the light chain variable regions comprise amino acid sequences having at least 80%, 85%, 90%, 95%, 98% 99% or 100% identity to (i) SEQ ID NOs: 67 and 80, respectively; (ii) SEQ ID NOs: 68 and 81, respectively; (iii) SEQ ID NOs: 69 and 81, respectively; (iv) SEQ ID NOs: 68 and 82, respectively; (v) SEQ ID NOs: 68 and 83, respectively; (vi) SEQ ID NOs: 68 and 84, respectively; (vii) SEQ ID NOs: 68 and 85, respectively; (viii) SEQ ID NOs: 68 and 86, respectively; (ix) SEQ ID NOs: 69 and 86, respectively; (x) SEQ ID NOs: 70 and 87 respectively; (xi) SEQ ID NOs: 71 and 88, respectively; (xii) SEQ ID NOs: 72 and 89, respectively; (xiii) SEQ ID NOs: 73 and 90, respectively; (xiv) SEQ ID NOs: 74 and 91, respectively; (xv) SEQ ID NOs: 75 and 92, respectively; (xvi) SEQ ID NOs: 76 and 93, respectively; (xvii) SEQ ID NOs: 77 and 94, respectively; (xviii) SEQ ID NOs: 78 and 95, respectively; or (xix) SEQ ID NOs: 79 and 96, respectively.

3. The isolated monoclonal antibody, or an antigen-binding portion thereof, of claim 1, wherein the heavy chain constant region comprises an amino acid sequence having at least 80%, 85%, 90%, 95%, 98% 99% or 100% identity to SEQ ID NOs: 97, 99 or 129, and/or the light chain constant region comprises an amino acid sequence having at least 80%, 85%, 90%, 95%, 98% 99% or 100% identity to SEQ ID NOs: 98 or 130.

4. The antibody, or the antigen-binding portion thereof, of claim 1, which (a) binds to human PD-1; (b) binds to monkey PD-1; (c) inhibits binding of PD-L1 to PD-1; (d) increases T cell proliferation; (e) stimulates an immune response; and/or (f) stimulates an antigen-specific T cell response.

5. The antibody, or the antigen-binding portion thereof, of claim 1, which is a mouse, chimeric or humanized antibody.

6. The antibody, or the antigen-binding portion thereof, of claim 1, which is an IgG4 IgG1, IgG2 or IgG4 isotype.

7. A pharmaceutical composition comprising the antibody, or antigen-binding portion thereof, of claim 1, and a pharmaceutically acceptable carrier.

8. A method for inhibiting tumor growth in a subject, comprising administering to the subject a therapeutically effective amount of the pharmaceutical composition of claim 7.

9. The method of claim 8, wherein the tumor is a solid or non-solid tumor.

10. The method of claim 8, wherein the tumor is selected from the group consisting of lymphoma, leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, renal-cell cancer and nasopharynx cancer.

* * * * *

SEQUENCE LISTING

<160> NUMBER OF SEQ ID NOS: 130

<210> SEQ ID NO 1
<211> LENGTH: 8
<212> TYPE: PRT
<213> ORGANISM: Artificial Sequence
<220> FEATURE:
<223> OTHER INFORMATION: VH-CDR1 for C1E1, huC1E1-V1 - huC1E1-V7 and
huC1E1-V10

<400> SEQUENCE: 1

Gly Phe Thr Phe Ser Ser Tyr Leu
1 5

<210> SEQ ID NO 2
<211> LENGTH: 8
<212> TYPE: PRT
<213> ORGANISM: Artificial Sequence
<220> FEATURE:
<223> OTHER INFORMATION: VH-CDR2 for C1E1, huC1E1-V1 - huC1E1-V7 and huC1E1-V10

<400> SEQUENCE: 2

Ile Ser Gly Gly Gly Gly Asp Thr
1 5

<210> SEQ ID NO 3
<211> LENGTH: 13
<212> TYPE: PRT
<213> ORGANISM: Artificial Sequence
<220> FEATURE:
<223> OTHER INFORMATION: VH-CDR3 for C1E1, huC1E1-V1 - huC1E1-V7 and huC1E1-V10

<400> SEQUENCE: 3

Val Arg Phe Gly Gly Ala Gly Tyr Tyr Trp Tyr Phe Asp
1 5 10

<210> SEQ ID NO 4
<211> LENGTH: 8
<212> TYPE: PRT
<213> ORGANISM: Artificial Sequence
<220> FEATURE:
<223> OTHER INFORMATION: VH-CDR1 for D1F2

<400> SEQUENCE: 4

Gly Phe Thr Phe Ser Ser Tyr Thr
1 5

<210> SEQ ID NO 5
<211> LENGTH: 8
<212> TYPE: PRT
<213> ORGANISM: Artificial Sequence
<220> FEATURE:
<223> OTHER INFORMATION: VH-CDR2 for D1F2

<400> SEQUENCE: 5

Ile Ser Gly Gly Gly Ser Asn Ile
1 5

<210> SEQ ID NO 6
<211> LENGTH: 13
<212> TYPE: PRT
<213> ORGANISM: Artificial Sequence
<220> FEATURE:
<223> OTHER INFORMATION: VH-CDR3 for D1F2

<400> SEQUENCE: 6

Val Leu Asn Tyr Ala Tyr Ala Met Asp Tyr Trp Gly Gln
1 5 10

<210> SEQ ID NO 7
<211> LENGTH: 8
<212> TYPE: PRT
<213> ORGANISM: Artificial Sequence
<220> FEATURE:

```
<223> OTHER INFORMATION: VH-CDR1 for C1F5

<400> SEQUENCE: 7

Gly Phe Ala Phe Ser Ser Tyr Asp
1               5


<210> SEQ ID NO 8
<211> LENGTH: 8
<212> TYPE: PRT
<213> ORGANISM: Artificial Sequence
<220> FEATURE:
<223> OTHER INFORMATION: VH-CDR2 for C1F5

<400> SEQUENCE: 8

Ile Thr Gly Gly Gly Ser Ser Ser
1               5


<210> SEQ ID NO 9
<211> LENGTH: 13
<212> TYPE: PRT
<213> ORGANISM: Artificial Sequence
<220> FEATURE:
<223> OTHER INFORMATION: VH-CDR3 for C1F5

<400> SEQUENCE: 9

Ala Ser Pro Tyr Leu Ser Tyr Phe Asp Tyr Trp Gly Gln
1               5                   10


<210> SEQ ID NO 10
<211> LENGTH: 8
<212> TYPE: PRT
<213> ORGANISM: Artificial Sequence
<220> FEATURE:
<223> OTHER INFORMATION: VH-CDR1 for D1A1

<400> SEQUENCE: 10

Gly Phe Thr Phe Ser Asn Tyr Ala
1               5


<210> SEQ ID NO 11
<211> LENGTH: 8
<212> TYPE: PRT
<213> ORGANISM: Artificial Sequence
<220> FEATURE:
<223> OTHER INFORMATION: VH-CDR2 for D1A1

<400> SEQUENCE: 11

Ile Ser Gly Gly Gly Gly Asn Ile
1               5


<210> SEQ ID NO 12
<211> LENGTH: 13
<212> TYPE: PRT
<213> ORGANISM: Artificial Sequence
<220> FEATURE:
<223> OTHER INFORMATION: VH-CDR3 for D1A1

<400> SEQUENCE: 12

Ala Ser Pro Tyr Ala Asn Tyr Val Trp Tyr Leu Asp Val
1               5                   10


<210> SEQ ID NO 13
<211> LENGTH: 8
<212> TYPE: PRT
<213> ORGANISM: Artificial Sequence
<220> FEATURE:
<223> OTHER INFORMATION: VH-CDR1 for D1F1
```

<400> SEQUENCE: 13

Gly Phe Thr Phe Ser Ser Asn Thr
1 5

<210> SEQ ID NO 14
<211> LENGTH: 8
<212> TYPE: PRT
<213> ORGANISM: Artificial Sequence
<220> FEATURE:
<223> OTHER INFORMATION: VH-CDR2 for D1F1

<400> SEQUENCE: 14

Ile Ser Gly Gly Gly Val Asn Thr
1 5

<210> SEQ ID NO 15
<211> LENGTH: 13
<212> TYPE: PRT
<213> ORGANISM: Artificial Sequence
<220> FEATURE:
<223> OTHER INFORMATION: VH-CDR3 for D1F1

<400> SEQUENCE: 15

Ala Arg His Gly Asn Tyr Asn Tyr Tyr Gly Met Asp Tyr
1 5 10

<210> SEQ ID NO 16
<211> LENGTH: 8
<212> TYPE: PRT
<213> ORGANISM: Artificial Sequence
<220> FEATURE:
<223> OTHER INFORMATION: VH-CDR1 for C1E2

<400> SEQUENCE: 16

Gly Tyr Thr Phe Thr Asn Tyr Trp
1 5

<210> SEQ ID NO 17
<211> LENGTH: 8
<212> TYPE: PRT
<213> ORGANISM: Artificial Sequence
<220> FEATURE:
<223> OTHER INFORMATION: VH-CDR2 for C1E2

<400> SEQUENCE: 17

Ile Tyr Pro Gly Gly Gly Tyr Thr
1 5

<210> SEQ ID NO 18
<211> LENGTH: 13
<212> TYPE: PRT
<213> ORGANISM: Artificial Sequence
<220> FEATURE:
<223> OTHER INFORMATION: VH-CDR3 for C1E2

<400> SEQUENCE: 18

Ala Arg Gly Tyr Gly Thr Asn Tyr Trp Tyr Phe Asp Val
1 5 10

<210> SEQ ID NO 19
<211> LENGTH: 10
<212> TYPE: PRT
<213> ORGANISM: Artificial Sequence
<220> FEATURE:
<223> OTHER INFORMATION: VH-CDR1 for C1A1

<400> SEQUENCE: 19

Gly Phe Ser Leu Ser Thr Ser Gly Met Gly
1               5                   10

<210> SEQ ID NO 20
<211> LENGTH: 7
<212> TYPE: PRT
<213> ORGANISM: Artificial Sequence
<220> FEATURE:
<223> OTHER INFORMATION: VH-CDR2 for C1A1

<400> SEQUENCE: 20

Ile Trp Trp Asp Asp Asp Lys
1               5

<210> SEQ ID NO 21
<211> LENGTH: 13
<212> TYPE: PRT
<213> ORGANISM: Artificial Sequence
<220> FEATURE:
<223> OTHER INFORMATION: VH-CDR3 for C1A1

<400> SEQUENCE: 21

Ala Arg Thr Gly Gly Phe Ile Thr Thr Gly Tyr Trp Tyr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: VH-CDR1 for C1F4

<400> SEQUENCE: 22

Gly Tyr Lys Phe Thr Asp Tyr Ala
1               5

<210> SEQ ID NO 23
<211> LENGTH: 8
<212> TYPE: PRT
<213> ORGANISM: Artificial Sequence
<220> FEATURE:
<223> OTHER INFORMATION: VH-CDR2 for C1F4

<400> SEQUENCE: 23

Ile Ser Thr Tyr Ser Gly Asp Val
1               5

<210> SEQ ID NO 24
<211> LENGTH: 13
<212> TYPE: PRT
<213> ORGANISM: Artificial Sequence
<220> FEATURE:
<223> OTHER INFORMATION: VH-CDR3 for C1F4

<400> SEQUENCE: 24

Ser Arg Leu Gly Ile Thr Ala Gly Phe Ala Tyr Trp Gly
1               5                   10

<210> SEQ ID NO 25
<211> LENGTH: 8
<212> TYPE: PRT
<213> ORGANISM: Artificial Sequence
<220> FEATURE:
<223> OTHER INFORMATION: VH-CDR1 for D2C2

<400> SEQUENCE: 25

Gly Phe Thr Phe Ser Ser Asn Thr
1 5

<210> SEQ ID NO 26
<211> LENGTH: 8
<212> TYPE: PRT
<213> ORGANISM: Artificial Sequence
<220> FEATURE:
<223> OTHER INFORMATION: VH-CDR2 for D2C2

<400> SEQUENCE: 26

Ile Ser Gly Gly Gly Val Asp Thr
1 5

<210> SEQ ID NO 27
<211> LENGTH: 13
<212> TYPE: PRT
<213> ORGANISM: Artificial Sequence
<220> FEATURE:
<223> OTHER INFORMATION: VH-CDR3 for D2C2

<400> SEQUENCE: 27

Ala Arg His Gly Asn Tyr Asn Tyr Tyr Gly Met Asp Tyr
1 5 10

<210> SEQ ID NO 28
<211> LENGTH: 8
<212> TYPE: PRT
<213> ORGANISM: Artificial Sequence
<220> FEATURE:
<223> OTHER INFORMATION: VH-CDR1 for 2G2

<400> SEQUENCE: 28

Gly Phe Thr Phe Ser Tyr Tyr Gly
1 5

<210> SEQ ID NO 29
<211> LENGTH: 8
<212> TYPE: PRT
<213> ORGANISM: Artificial Sequence
<220> FEATURE:
<223> OTHER INFORMATION: VH-CDR2 for 2G2

<400> SEQUENCE: 29

Ile Ser Ser Gly Ser Ser Phe Thr
1 5

<210> SEQ ID NO 30
<211> LENGTH: 13
<212> TYPE: PRT
<213> ORGANISM: Artificial Sequence
<220> FEATURE:
<223> OTHER INFORMATION: VH-CDR3 for 2G2

<400> SEQUENCE: 30

Thr Arg Arg Glu Gly Ile Tyr Asp Ala Ser Trp Asp Tyr
1 5 10

<210> SEQ ID NO 31
<211> LENGTH: 8
<212> TYPE: PRT
<213> ORGANISM: Artificial Sequence
<220> FEATURE:
<223> OTHER INFORMATION: VH-CDR1 for C1C5

<400> SEQUENCE: 31

Gly Tyr Thr Phe Thr Asn Tyr Gly
1 5

<210> SEQ ID NO 32
<211> LENGTH: 8
<212> TYPE: PRT
<213> ORGANISM: Artificial Sequence
<220> FEATURE:
<223> OTHER INFORMATION: VH-CDR2 for C1C5

<400> SEQUENCE: 32

Ile Asn Thr Tyr Ser Gly Glu Pro
1 5

<210> SEQ ID NO 33
<211> LENGTH: 13
<212> TYPE: PRT
<213> ORGANISM: Artificial Sequence
<220> FEATURE:
<223> OTHER INFORMATION: VH-CDR3 for C1C5

<400> SEQUENCE: 33

Val Arg Gln Gly Asp Phe Asp Tyr Glu Asp Ala Met Asp
1 5 10

<210> SEQ ID NO 34
<211> LENGTH: 15
<212> TYPE: PRT
<213> ORGANISM: Artificial Sequence
<220> FEATURE:
<223> OTHER INFORMATION: VL-CDR1 for C1E1, huC1E1-V1 - huC1E1-V7 and huC1E1-V10

<400> SEQUENCE: 34

Arg Ala Ser Lys Ser Val Asp Asp Ser Gly Ile Ser Phe Met His
1 5 10 15

<210> SEQ ID NO 35
<211> LENGTH: 7
<212> TYPE: PRT
<213> ORGANISM: Artificial Sequence
<220> FEATURE:
<223> OTHER INFORMATION: VL-CDR2 for C1E1, huC1E1-V1 - huC1E1-V7 and huC1E1-V10

<400> SEQUENCE: 35

Ala Ala Ser Asn Gln Gly Ser
1 5

<210> SEQ ID NO 36
<211> LENGTH: 9
<212> TYPE: PRT
<213> ORGANISM: Artificial Sequence
<220> FEATURE:
<223> OTHER INFORMATION: VL-CDR3 for C1E1, huC1E1-V1 - huC1E1-V7 and huC1E1-V10

<400> SEQUENCE: 36

His Gln Thr Lys Glu Val Pro Trp Thr
1 5

<210> SEQ ID NO 37
<211> LENGTH: 11
<212> TYPE: PRT
<213> ORGANISM: Artificial Sequence
<220> FEATURE:
<223> OTHER INFORMATION: VL-CDR1 for D1F2

<400> SEQUENCE: 37

Arg Ala Ser Gln Asp Ile Ser Asn Phe Leu Asn
1 5 10

<210> SEQ ID NO 38
<211> LENGTH: 7
<212> TYPE: PRT
<213> ORGANISM: Artificial Sequence
<220> FEATURE:
<223> OTHER INFORMATION: VL-CDR2 for D1F2

<400> SEQUENCE: 38

Tyr Thr Ser Arg Leu Gln Ser
1 5

<210> SEQ ID NO 39
<211> LENGTH: 9
<212> TYPE: PRT
<213> ORGANISM: Artificial Sequence
<220> FEATURE:
<223> OTHER INFORMATION: VL-CDR3 for D1F2

<400> SEQUENCE: 39

Gln Gln Gly Ser Ser Leu Pro Trp Thr
1 5

<210> SEQ ID NO 40
<211> LENGTH: 11
<212> TYPE: PRT
<213> ORGANISM: Artificial Sequence
<220> FEATURE:
<223> OTHER INFORMATION: VL-CDR1 for C1F5

<400> SEQUENCE: 40

Arg Ala Ser Gln Ser Ile Ser Asn Asn Leu His
1 5 10

<210> SEQ ID NO 41
<211> LENGTH: 6
<212> TYPE: PRT
<213> ORGANISM: Artificial Sequence
<220> FEATURE:
<223> OTHER INFORMATION: VL-CDR2 for C1F5

<400> SEQUENCE: 41

Gly Ser Gln Ser Met Ser
1 5

<210> SEQ ID NO 42
<211> LENGTH: 9
<212> TYPE: PRT
<213> ORGANISM: Artificial Sequence
<220> FEATURE:
<223> OTHER INFORMATION: VL-CDR3 for C1F5

<400> SEQUENCE: 42

Gln Gln Ser Asn Ser Trp Pro Leu Thr
1 5

<210> SEQ ID NO 43
<211> LENGTH: 11
<212> TYPE: PRT
<213> ORGANISM: Artificial Sequence
<220> FEATURE:
<223> OTHER INFORMATION: VL-CDR1 for D1A1

<400> SEQUENCE: 43

Arg Ala Ser Gln Asp Ile Ser Asn Tyr Leu Asn
1 5 10

<210> SEQ ID NO 44
<211> LENGTH: 7
<212> TYPE: PRT
<213> ORGANISM: Artificial Sequence
<220> FEATURE:
<223> OTHER INFORMATION: VL-CDR3 for D1A1

<400> SEQUENCE: 44

Tyr Thr Ser Arg Leu His Ser
1 5

<210> SEQ ID NO 45
<211> LENGTH: 9
<212> TYPE: PRT
<213> ORGANISM: Artificial Sequence
<220> FEATURE:
<223> OTHER INFORMATION: VL-CDR3 for D1A1

<400> SEQUENCE: 45

Gln Gln Ser Asn Ala Leu Pro Trp Thr
1 5

<210> SEQ ID NO 46
<211> LENGTH: 15
<212> TYPE: PRT
<213> ORGANISM: Artificial Sequence
<220> FEATURE:
<223> OTHER INFORMATION: VL-CDR1 for D1F1

<400> SEQUENCE: 46

Arg Ala Ser Glu Ser Val Asp Asn Ser Gly Ile Ser Phe Met Asn
1 5 10 15

<210> SEQ ID NO 47
<211> LENGTH: 7
<212> TYPE: PRT
<213> ORGANISM: Artificial Sequence
<220> FEATURE:
<223> OTHER INFORMATION: VL-CDR2 for D1F1

<400> SEQUENCE: 47

Thr Ala Ser Asn Gln Gly Ser
1 5

<210> SEQ ID NO 48
<211> LENGTH: 9
<212> TYPE: PRT
<213> ORGANISM: Artificial Sequence
<220> FEATURE:
<223> OTHER INFORMATION: VL-CDR3 for D1F1

<400> SEQUENCE: 48

Gln Gln Ser Tyr Glu Val Pro Trp Thr
1 5

<210> SEQ ID NO 49
<211> LENGTH: 11
<212> TYPE: PRT
<213> ORGANISM: Artificial Sequence
<220> FEATURE:
<223> OTHER INFORMATION: VL-CDR1 for C1E2

<400> SEQUENCE: 49

Lys Ala Ser Gln Ser Val Ser Asn Asp Val Ala
1 5 10

<210> SEQ ID NO 50
<211> LENGTH: 7
<212> TYPE: PRT
<213> ORGANISM: Artificial Sequence
<220> FEATURE:
<223> OTHER INFORMATION: VL-CDR2 for C1E2

<400> SEQUENCE: 50

Tyr Ala Phe His Arg Tyr Thr
1 5

<210> SEQ ID NO 51
<211> LENGTH: 9
<212> TYPE: PRT
<213> ORGANISM: Artificial Sequence
<220> FEATURE:
<223> OTHER INFORMATION: VL-CDR3 for C1E2

<400> SEQUENCE: 51

Gln Gln Asp Tyr Ser Ser Pro Tyr Thr
1 5

<210> SEQ ID NO 52
<211> LENGTH: 11
<212> TYPE: PRT
<213> ORGANISM: Artificial Sequence
<220> FEATURE:
<223> OTHER INFORMATION: VL-CDR1 for C1A1

<400> SEQUENCE: 52

Arg Ala Ser Gln Asp Ile Ser Asn Tyr Leu Ile
1 5 10

<210> SEQ ID NO 53
<211> LENGTH: 7
<212> TYPE: PRT
<213> ORGANISM: Artificial Sequence
<220> FEATURE:
<223> OTHER INFORMATION: VL-CDR2 for C1A1

<400> SEQUENCE: 53

Tyr Thr Ser Arg Leu His Ser
1 5

<210> SEQ ID NO 54
<211> LENGTH: 9
<212> TYPE: PRT
<213> ORGANISM: Artificial Sequence
<220> FEATURE:
<223> OTHER INFORMATION: VL-CDR3 for C1A1

<400> SEQUENCE: 54

Gln Gln His Lys Thr Leu Pro Trp Thr
1 5

<210> SEQ ID NO 55
<211> LENGTH: 11
<212> TYPE: PRT
<213> ORGANISM: Artificial Sequence
<220> FEATURE:
<223> OTHER INFORMATION: VL-CDR1 for C1F4

<400> SEQUENCE: 55

Lys Ala Ser Gln Asn Val Arg Thr Ala Val Ala 1 5 10

<210> SEQ ID NO 56
<211> LENGTH: 7
<212> TYPE: PRT
<213> ORGANISM: Artificial Sequence
<220> FEATURE:
<223> OTHER INFORMATION: VL-CDR2 for C1F4

<400> SEQUENCE: 56

Leu Ala Ser Asn Arg His Thr
1 5

<210> SEQ ID NO 57
<211> LENGTH: 9
<212> TYPE: PRT
<213> ORGANISM: Artificial Sequence
<220> FEATURE:
<223> OTHER INFORMATION: VL-CDR3 for C1F4

<400> SEQUENCE: 57

Leu Gln His Trp Asn Tyr Pro Tyr Thr
1 5

<210> SEQ ID NO 58
<211> LENGTH: 15
<212> TYPE: PRT
<213> ORGANISM: Artificial Sequence
<220> FEATURE:
<223> OTHER INFORMATION: VL-CDR1 for D2C2

<400> SEQUENCE: 58

Arg Ala Ser Glu Ser Val Asp Asn Ser Gly Ile Ser Phe Met Asn
1 5 10 15

<210> SEQ ID NO 59
<211> LENGTH: 7
<212> TYPE: PRT
<213> ORGANISM: Artificial Sequence
<220> FEATURE:
<223> OTHER INFORMATION: VL-CDR2 for D2C2

<400> SEQUENCE: 59

Ile Ala Ser Asn His Gly Ser
1 5

<210> SEQ ID NO 60
<211> LENGTH: 9
<212> TYPE: PRT
<213> ORGANISM: Artificial Sequence
<220> FEATURE:
<223> OTHER INFORMATION: VL-CDR3 for D2C2

<400> SEQUENCE: 60

Gln Gln Ser Tyr Glu Val Pro Trp Thr
1 5

<210> SEQ ID NO 61
<211> LENGTH: 16
<212> TYPE: PRT
<213> ORGANISM: Artificial Sequence
<220> FEATURE:
<223> OTHER INFORMATION: VL-CDR1 for 2G2

<400> SEQUENCE: 61

Arg Ser Ser Gln Ser Ile Ile Arg Ser Asn Gly Asn Thr Tyr Leu Glu
1 5 10 15

-continued

<210> SEQ ID NO 62
<211> LENGTH: 7
<212> TYPE: PRT
<213> ORGANISM: Artificial Sequence
<220> FEATURE:
<223> OTHER INFORMATION: VL-CDR2 for 2G2

<400> SEQUENCE: 62

Lys Val Ser Asn Arg Phe Ser
1 5

<210> SEQ ID NO 63
<211> LENGTH: 9
<212> TYPE: PRT
<213> ORGANISM: Artificial Sequence
<220> FEATURE:
<223> OTHER INFORMATION: VL-CDR3 for 2G2

<400> SEQUENCE: 63

Phe Gln Gly Ser His Val Pro Trp Thr
1 5

<210> SEQ ID NO 64
<211> LENGTH: 16
<212> TYPE: PRT
<213> ORGANISM: Artificial Sequence
<220> FEATURE:
<223> OTHER INFORMATION: VL-CDR1 for C1C5

<400> SEQUENCE: 64

Arg Ser Ser Gln Ser Ile Val His Ser Asn Gly His Ile Tyr Leu Glu
1 5 10 15

<210> SEQ ID NO 65
<211> LENGTH: 7
<212> TYPE: PRT
<213> ORGANISM: Artificial Sequence
<220> FEATURE:
<223> OTHER INFORMATION: VL-CDR2 for C1C5

<400> SEQUENCE: 65

Lys Val Ser Lys Arg Phe Ser
1 5

<210> SEQ ID NO 66
<211> LENGTH: 7
<212> TYPE: PRT
<213> ORGANISM: Artificial Sequence
<220> FEATURE:
<223> OTHER INFORMATION: VL-CDR3 for C1C5

<400> SEQUENCE: 66

Phe Gln Gly Ser His Gly Thr
1 5

<210> SEQ ID NO 67
<211> LENGTH: 121
<212> TYPE: PRT
<213> ORGANISM: Artificial Sequence
<220> FEATURE:
<223> OTHER INFORMATION: VH for C1E1

<400> SEQUENCE: 67

Glu Val Met Leu Val Glu Ser Gly Gly Gly Leu Val Lys Pro Gly Gly
1 5 10 15

```
Ser Leu Lys Leu Ser Cys Ala Ala Ser Gly Phe Thr Phe Ser Ser Tyr
            20                  25                  30

Leu Met Ser Trp Val Arg Gln Thr Pro Glu Lys Arg Leu Glu Trp Val
        35                  40                  45

Ala Thr Ile Ser Gly Gly Gly Gly Asp Thr Tyr Phe Pro Asp Ser Val
    50                  55                  60

Lys Gly Arg Phe Thr Ile Ser Arg Asp Asn Val Lys Asn Asn Leu Tyr
65                  70                  75                  80

Leu Gln Met Ser Ser Leu Arg Ser Glu Asp Thr Ala Leu Tyr Tyr Cys
                85                  90                  95

Val Arg Phe Gly Gly Ala Gly Tyr Tyr Trp Tyr Phe Asp Val Trp Gly
            100                 105                 110

Ala Gly Thr Thr Val Thr Val Ser Ser
        115                 120


<210> SEQ ID NO 68
<211> LENGTH: 121
<212> TYPE: PRT
<213> ORGANISM: Artificial Sequence
<220> FEATURE:
<223> OTHER INFORMATION: VH for huC1E1-V1, huC1E1-V3 - huC1E1-V7

<400> SEQUENCE: 68

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ala Thr Ile Ser Gly Gly Gly Gly Asp Thr Tyr Phe Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Phe Gly Gly Ala Gly Tyr Tyr Trp Tyr Phe Asp Val Trp Gly
            100                 105                 110

Ala Gly Thr Leu Val Thr Val Ser Ser
        115                 120


<210> SEQ ID NO 69
<211> LENGTH: 121
<212> TYPE: PRT
<213> ORGANISM: Artificial Sequence
<220> FEATURE:
<223> OTHER INFORMATION: VH for huC1E1-V2 and huC1E1-V10

<400> SEQUENCE: 69

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ala Thr Ile Ser Gly Gly Gly Gly Asp Thr Tyr Phe Pro Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Val Arg Phe Gly Gly Ala Gly Tyr Tyr Trp Tyr Phe Asp Val Trp Gly
            100                 105                 110

Gln Gly Thr Leu Val Thr Val Ser Ser
        115                 120


<210> SEQ ID NO 70
<211> LENGTH: 117
<212> TYPE: PRT
<213> ORGANISM: Artificial Sequence
<220> FEATURE:
<223> OTHER INFORMATION: VH for D1F2

<400> SEQUENCE: 70

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Ser Asn Ile Tyr Tyr Pro Asp Ser Val
    50                  55                  60

Glu Gly Arg Phe Thr Val Ser Arg Asp Asn Ala Arg Asn Thr Leu Tyr
65                  70                  75                  80

Leu His Met Ser Ser Leu Arg Ser Glu Asp Thr Ala Leu Tyr Tyr Cys
                85                  90                  95

Val Leu Asn Tyr Ala Tyr Ala Met Asp Tyr Trp Gly Gln Gly Thr Ser
            100                 105                 110

Val Thr Val Ser Ser
        115


<210> SEQ ID NO 71
<211> LENGTH: 117
<212> TYPE: PRT
<213> ORGANISM: Artificial Sequence
<220> FEATURE:
<223> OTHER INFORMATION: VH for C1F5

<400> SEQUENCE: 71

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Thr Gly Gly Gly Ser Ser Ser Phe Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Ser Glu Asp Thr Ala Met Tyr Tyr Cys
                85                  90                  95

Ala Ser Pro Tyr Leu Ser Tyr Phe Asp Tyr Trp Gly Gln Gly Thr Thr
            100                 105                 110

Leu Thr Val Ser Ser
        115
```

<210> SEQ ID NO 72
<211> LENGTH: 120
<212> TYPE: PRT
<213> ORGANISM: Artificial Sequence
<220> FEATURE:
<223> OTHER INFORMATION: VH for D1A1

<400> SEQUENCE: 72

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Gly Gly Gly Gly Asn Ile Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Ser Pro Tyr Ala Asn Tyr Val Trp Tyr Leu Asp Val Trp Gly Ala
            100                 105                 110

Gly Thr Thr Val Thr Val Ser Ser
        115                 120
```

<210> SEQ ID NO 73
<211> LENGTH: 120
<212> TYPE: PRT
<213> ORGANISM: Artificial Sequence
<220> FEATURE:
<223> OTHER INFORMATION: VH for D1F1

<400> SEQUENCE: 73

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Asn
            20                  25                  30

Thr Met Ser Trp Val Arg Gln Thr Pro Glu Lys Arg Leu Glu Trp Val
        35                  40                  45

Ala Ala Ile Ser Gly Gly Gly Val Asn Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg His Gly Asn Tyr Asn Tyr Tyr Gly Met Asp Tyr Trp Gly Gln
            100                 105                 110

Gly Thr Ser Val Thr Val Ser Ser
        115                 120
```

<210> SEQ ID NO 74
<211> LENGTH: 120
<212> TYPE: PRT
<213> ORGANISM: Artificial Sequence
<220> FEATURE:
<223> OTHER INFORMATION: VH for C1E2

<400> SEQUENCE: 74

```
Gln Val Gln Leu Gln Gln Ser Gly Ala Glu Leu Val Arg Pro Gly Thr
1               5                   10                  15
```

```
Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Asn Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Phe Phe Cys
                85                  90                  95

Ala Arg Gly Tyr Gly Thr Asn Tyr Trp Tyr Phe Asp Val Trp Gly Ala
            100                 105                 110

Gly Thr Thr Val Thr Val Ser Ser
        115                 120


<210> SEQ ID NO 75
<211> LENGTH: 124
<212> TYPE: PRT
<213> ORGANISM: Artificial Sequence
<220> FEATURE:
<223> OTHER INFORMATION: VH for C1A1

<400> SEQUENCE: 75

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Phe Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Thr Gly Gly Phe Ile Thr Thr Gly Tyr Trp Tyr Phe Asp
            100                 105                 110

Val Trp Gly Ala Gly Thr Thr Val Thr Val Ser Ser
        115                 120


<210> SEQ ID NO 76
<211> LENGTH: 118
<212> TYPE: PRT
<213> ORGANISM: Artificial Sequence
<220> FEATURE:
<223> OTHER INFORMATION: VH for C1F4

<400> SEQUENCE: 76

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Lys Phe Thr Asp Tyr
            20                  25                  30

Ala Met His Trp Val Arg Gln Ser His Ala Lys Ser Leu Glu Trp Ile
        35                  40                  45

Gly Ile Ile Ser Thr Tyr Ser Gly Asp Val Ser Phe Asn Gln Asn Phe
    50                  55                  60

Lys Gly Lys Ala Thr Met Thr Val Asp Lys Ser Ser Ser Thr Ala Tyr
```

```
65                  70                  75                  80

Met Glu Leu Ala Arg Leu Thr Ser Glu Asp Ser Ala Ile Tyr Tyr Cys
                85                  90                  95

Ser Arg Leu Gly Ile Thr Ala Gly Phe Ala Tyr Trp Gly Gln Gly Thr
            100                 105                 110

Leu Val Thr Val Ser Ala
        115


<210> SEQ ID NO 77
<211> LENGTH: 120
<212> TYPE: PRT
<213> ORGANISM: Artificial Sequence
<220> FEATURE:
<223> OTHER INFORMATION: VH for D2C2

<400> SEQUENCE: 77

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Asn
            20                  25                  30

Thr Met Ser Trp Val Arg Gln Thr Pro Glu Lys Arg Leu Glu Trp Val
        35                  40                  45

Ala Ala Ile Ser Gly Gly Gly Val Asp Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg His Gly Asn Tyr Asn Tyr Tyr Gly Met Asp Tyr Trp Gly Gln
            100                 105                 110

Gly Thr Ser Val Thr Val Ser Ser
        115                 120


<210> SEQ ID NO 78
<211> LENGTH: 124
<212> TYPE: PRT
<213> ORGANISM: Artificial Sequence
<220> FEATURE:
<223> OTHER INFORMATION: VH for 2G2

<400> SEQUENCE: 78

Glu Val Gln Leu Val Glu Ser Gly Gly Asp Leu Val Lys Pro Gly Gly
1               5                   10                  15

Ser Leu Lys Leu Ser Cys Thr Ala Ser Gly Phe Thr Phe Ser Tyr Tyr
            20                  25                  30

Gly Met Ser Trp Val Arg Gln Thr Pro Asp Lys Arg Leu Glu Trp Val
        35                  40                  45

Ala Thr Ile Ser Ser Gly Ser Ser Phe Thr Tyr Ser Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Ile Tyr Tyr Cys
                85                  90                  95

Thr Arg Arg Glu Gly Ile Tyr Asp Ala Ser Trp Asp Tyr Ser Met Asp
            100                 105                 110

Tyr Trp Gly Gln Gly Thr Ser Val Thr Val Ser Ser
        115                 120
```

<210> SEQ ID NO 79
<211> LENGTH: 121
<212> TYPE: PRT
<213> ORGANISM: Artificial Sequence
<220> FEATURE:
<223> OTHER INFORMATION: VH for C1C5

<400> SEQUENCE: 79

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Ile Asn Trp Val Lys Gln Ala Pro Gly Lys Gly Leu Lys Trp Met
        35                  40                  45

Gly Trp Ile Asn Thr Tyr Ser Gly Glu Pro Thr Tyr Ser Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ser Thr Tyr Phe Cys
                85                  90                  95

Val Arg Gln Gly Asp Phe Asp Tyr Glu Asp Ala Met Asp Tyr Trp Gly
            100                 105                 110

Gln Gly Thr Ser Val Thr Val Ser Ser
        115                 120
```

<210> SEQ ID NO 80
<211> LENGTH: 111
<212> TYPE: PRT
<213> ORGANISM: Artificial Sequence
<220> FEATURE:
<223> OTHER INFORMATION: VL for C1E1

<400> SEQUENCE: 80

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Asp Asp Ser
            20                  25                  30

Gly Ile Ser Phe Met His Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Arg Gly Ser Gly Ser Gly Thr Asp Phe Ser Leu Asn Ile His
65                  70                  75                  80

Pro Met Glu Glu Asp Asp Thr Ala Met Tyr Phe Cys His Gln Thr Lys
                85                  90                  95

Glu Val Pro Trp Thr Phe Gly Gly Gly Thr Lys Leu Glu Ile Lys
            100                 105                 110
```

<210> SEQ ID NO 81
<211> LENGTH: 111
<212> TYPE: PRT
<213> ORGANISM: Artificial Sequence
<220> FEATURE:
<223> OTHER INFORMATION: VL for huC1E1-V1 and huC1E1-V2

<400> SEQUENCE: 81

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Asp Asp Ser
```

```
            20                  25                  30

Gly Ile Ser Phe Met His Trp Phe Gln Gln Lys Pro Gly Gln Pro Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys His Gln Thr Lys
                85                  90                  95

Glu Val Pro Trp Thr Phe Gly Gln Gly Thr Lys Val Glu Ile Lys
            100                 105                 110


<210> SEQ ID NO 82
<211> LENGTH: 111
<212> TYPE: PRT
<213> ORGANISM: Artificial Sequence
<220> FEATURE:
<223> OTHER INFORMATION: VL for huC1E1-V3

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Asp Asp Ser
            20                  25                  30

Gly Ile Ser Phe Met His Trp Tyr Gln Gln Lys Pro Gly Gln Pro Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys His Gln Thr Lys
                85                  90                  95

Glu Val Pro Trp Thr Phe Gly Gln Gly Thr Lys Val Glu Ile Lys
            100                 105                 110


<210> SEQ ID NO 83
<211> LENGTH: 111
<212> TYPE: PRT
<213> ORGANISM: Artificial Sequence
<220> FEATURE:
<223> OTHER INFORMATION: VL for huC1E1-V4

<400> SEQUENCE: 83

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Asp Asp Ser
            20                  25                  30

Gly Ile Ser Phe Met His Trp Phe Gln Gln Lys Pro Gly Gln Ala Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys His Gln Thr Lys
                85                  90                  95

Glu Val Pro Trp Thr Phe Gly Gln Gly Thr Lys Val Glu Ile Lys
            100                 105                 110
```

<210> SEQ ID NO 84
<211> LENGTH: 111
<212> TYPE: PRT
<213> ORGANISM: Artificial Sequence
<220> FEATURE:
<223> OTHER INFORMATION: VL for huC1E1-V5

<400> SEQUENCE: 84

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Asp Asp Ser
            20                  25                  30

Gly Ile Ser Phe Met His Trp Phe Gln Gln Lys Pro Gly Gln Pro Pro
        35                  40                  45

Arg Leu Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys His Gln Thr Lys
                85                  90                  95

Glu Val Pro Trp Thr Phe Gly Gln Gly Thr Lys Val Glu Ile Lys
            100                 105                 110
```

<210> SEQ ID NO 85
<211> LENGTH: 111
<212> TYPE: PRT
<213> ORGANISM: Artificial Sequence
<220> FEATURE:
<223> OTHER INFORMATION: VL for huC1E1-V6

<400> SEQUENCE: 85

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Asp Asp Ser
            20                  25                  30

Gly Ile Ser Phe Met His Trp Phe Gln Gln Lys Pro Gly Gln Pro Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Gln Thr Lys
                85                  90                  95

Glu Val Pro Trp Thr Phe Gly Gln Gly Thr Lys Val Glu Ile Lys
            100                 105                 110
```

<210> SEQ ID NO 86
<211> LENGTH: 111
<212> TYPE: PRT
<213> ORGANISM: Artificial Sequence
<220> FEATURE:
<223> OTHER INFORMATION: VL for huC1E1-V7 and huC1E1-V10

<400> SEQUENCE: 86

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Asp Asp Ser
            20                  25                  30

Gly Ile Ser Phe Met His Trp Tyr Gln Gln Lys Pro Gly Gln Ala Pro
```

```
        35                  40                  45

Arg Leu Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Gln Thr Lys
                85                  90                  95

Glu Val Pro Trp Thr Phe Gly Gln Gly Thr Lys Val Glu Ile Lys
            100                 105                 110


<210> SEQ ID NO 87
<211> LENGTH: 107
<212> TYPE: PRT
<213> ORGANISM: Artificial Sequence
<220> FEATURE:
<223> OTHER INFORMATION: VL for D1F2

<400> SEQUENCE: 87

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Thr Gly Ser Gly Thr Asp Tyr Ser Leu Thr Ile Ser Asn Leu Glu Gln
65                  70                  75                  80

Glu Asp Leu Ala Thr Tyr Phe Cys Gln Gln Gly Ser Ser Leu Pro Trp
                85                  90                  95

Thr Phe Gly Gly Gly Thr Lys Leu Glu Ile Lys
            100                 105


<210> SEQ ID NO 88
<211> LENGTH: 107
<212> TYPE: PRT
<213> ORGANISM: Artificial Sequence
<220> FEATURE:
<223> OTHER INFORMATION: VL for C1F5

<400> SEQUENCE: 88

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Gly Ser Gln Ser Met Ser Gly Ile Pro Ser Arg Phe Ser Gly
    50                  55                  60

Ser Gly Ser Gly Thr Asp Phe Thr Leu Val Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105


<210> SEQ ID NO 89
<211> LENGTH: 107
```

<212> TYPE: PRT
<213> ORGANISM: Artificial Sequence
<220> FEATURE:
<223> OTHER INFORMATION: VL for D1A1

<400> SEQUENCE: 89

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Glu
65                  70                  75                  80

Glu Asp Ile Ala Thr Tyr Phe Cys Gln Gln Ser Asn Ala Leu Pro Trp
                85                  90                  95

Thr Phe Gly Gly Gly Thr Lys Leu Glu Ile Lys
            100                 105
```

<210> SEQ ID NO 90
<211> LENGTH: 111
<212> TYPE: PRT
<213> ORGANISM: Artificial Sequence
<220> FEATURE:
<223> OTHER INFORMATION: VL for D1F1

<400> SEQUENCE: 90

```
Asp Ile Val Leu Thr Gln Ser Pro Ala Ser Leu Val Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met Asn Trp Phe Gln Gln Lys Pro Gly Gln Pro Pro
        35                  40                  45

Lys Leu Leu Ile Tyr Thr Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ser Ala Met Tyr Phe Cys Gln Gln Ser Tyr
                85                  90                  95

Glu Val Pro Trp Thr Phe Gly Gly Gly Thr Lys Leu Glu Ile Lys
            100                 105                 110
```

<210> SEQ ID NO 91
<211> LENGTH: 107
<212> TYPE: PRT
<213> ORGANISM: Artificial Sequence
<220> FEATURE:
<223> OTHER INFORMATION: VL for C1E2

<400> SEQUENCE: 91

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Phe His Arg Tyr Thr Gly Val Pro Asp Arg Phe Thr Gly
```

```
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105


<210> SEQ ID NO 92
<211> LENGTH: 107
<212> TYPE: PRT
<213> ORGANISM: Artificial Sequence
<220> FEATURE:
<223> OTHER INFORMATION: VL for C1A1

<400> SEQUENCE: 92

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ile Trp Tyr Gln Gln Lys Thr Asp Gly Thr Leu Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln His Lys Thr Leu Pro Trp
                85                  90                  95

Thr Phe Gly Gly Gly Thr Lys Leu Glu Ile Lys
            100                 105


<210> SEQ ID NO 93
<211> LENGTH: 107
<212> TYPE: PRT
<213> ORGANISM: Artificial Sequence
<220> FEATURE:
<223> OTHER INFORMATION: VL for C1F4

<400> SEQUENCE: 93

Asp Ile Val Met Thr Gln Ser Gln Lys Phe Met Ser Thr Ser Val Gly
1               5                   10                  15

Asp Arg Val Thr Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Lys Asp Leu Ala Asp Tyr Phe Cys Leu Gln His Trp Asn Tyr Pro Tyr
                85                  90                  95

Thr Phe Gly Gly Gly Thr Lys Leu Glu Ile Lys
            100                 105


<210> SEQ ID NO 94
<211> LENGTH: 111
<212> TYPE: PRT
<213> ORGANISM: Artificial Sequence
<220> FEATURE:
```

<223> OTHER INFORMATION: VL for D2C2

<400> SEQUENCE: 94

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Asn Ser
20 25 30

Gly Ile Ser Phe Met Asn Trp Phe Gln Gln Lys Pro Gly Gln Ser Pro
35 40 45

Lys Leu Leu Ile Tyr Ile Ala Ser Asn His Gly Ser Gly Val Pro Ala
50 55 60

Arg Phe Ser Gly Ser Gly Ser Gly Thr Asp Phe Ser Leu Asn Ile His
65 70 75 80

Pro Met Glu Glu Asp Asp Ser Ala Met Tyr Phe Cys Gln Gln Ser Tyr
85 90 95

Glu Val Pro Trp Thr Phe Gly Gly Gly Thr Lys Leu Glu Ile Lys
100 105 110

<210> SEQ ID NO 95
<211> LENGTH: 112
<212> TYPE: PRT
<213> ORGANISM: Artificial Sequence
<220> FEATURE:
<223> OTHER INFORMATION: VL for 2G2

<400> SEQUENCE: 95

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Ile Arg Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Asp Asp Leu Gly Leu Tyr Tyr Cys Phe Gln Gly
85 90 95

Ser His Val Pro Trp Thr Phe Gly Gly Gly Thr Lys Leu Glu Ile Lys
100 105 110

<210> SEQ ID NO 96
<211> LENGTH: 110
<212> TYPE: PRT
<213> ORGANISM: Artificial Sequence
<220> FEATURE:
<223> OTHER INFORMATION: VL for C1C5

<400> SEQUENCE: 96

Asp Val Leu Met Thr Gln Ser Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly His Ile Tyr Leu Glu Trp Tyr Leu Gln Lys Pro Gly Gln Ser
35 40 45

Pro Lys Leu Leu Ile Tyr Lys Val Ser Lys Arg Phe Ser Gly Val Pro
50 55 60

Asp Arg Phe Ser Gly Ser Gly Ser Gly Thr Asp Phe Thr Leu Lys Ile

```
65                  70                  75                  80

Ser Arg Val Glu Ala Glu Asp Leu Gly Val Tyr Tyr Cys Phe Gln Gly
                85                  90                  95

Ser His Gly Thr Phe Gly Gly Gly Thr Lys Leu Glu Ile Lys
            100                 105                 110


<210> SEQ ID NO 97
<211> LENGTH: 330
<212> TYPE: PRT
<213> ORGANISM: Artificial Sequence
<220> FEATURE:
<223> OTHER INFORMATION: human IgG1 heavy chain constant region

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

325 330

<210> SEQ ID NO 98
<211> LENGTH: 107
<212> TYPE: PRT
<213> ORGANISM: Artificial Sequence
<220> FEATURE:
<223> OTHER INFORMATION: human kappa light chain constant region

<400> SEQUENCE: 98

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 99
<211> LENGTH: 98
<212> TYPE: PRT
<213> ORGANISM: Artificial Sequence
<220> FEATURE:
<223> OTHER INFORMATION: human IgG1 heavy chain CH1 region

<400> SEQUENCE: 99

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 100
<211> LENGTH: 371
<212> TYPE: PRT
<213> ORGANISM: Homo sapiens

<400> SEQUENCE: 100

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Ser Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Cys Arg Phe Arg Val Thr Gln Leu Pro Asn Gly Arg
65 70 75 80

Asp Phe His Met Ser Val Val Arg Ala Arg Arg Asn Asp Ser Gly Thr
85 90 95

Tyr Leu Cys Gly Ala Ile Ser Leu Ala Pro Lys Ala Gln Ile Lys Glu
100 105 110

Ser Leu Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln Glu
130 135 140

Pro Lys Ser Cys Asp Lys Thr His Thr Cys Pro Pro Cys Pro Ala Pro
145 150 155 160

Glu Leu Leu Gly Gly Pro Ser Val Phe Leu Phe Pro Pro Lys Pro Lys
165 170 175

Asp Thr Leu Met Ile Ser Arg Thr Pro Glu Val Thr Cys Val Val Val
180 185 190

Asp Val Ser His Glu Asp Pro Glu Val Lys Phe Asn Trp Tyr Val Asp
195 200 205

Gly Val Glu Val His Asn Ala Lys Thr Lys Pro Arg Glu Glu Gln Tyr
210 215 220

Asn Ser Thr Tyr Arg Val Val Ser Val Leu Thr Val Leu His Gln Asp
225 230 235 240

Trp Leu Asn Gly Lys Glu Tyr Lys Cys Lys Val Ser Asn Lys Ala Leu
245 250 255

Pro Ala Pro Ile Glu Lys Thr Ile Ser Lys Ala Lys Gly Gln Pro Arg
260 265 270

Glu Pro Gln Val Tyr Thr Leu Pro Pro Ser Arg Glu Glu Met Thr Lys
275 280 285

Asn Gln Val Ser Leu Thr Cys Leu Val Lys Gly Phe Tyr Pro Ser Asp
290 295 300

Ile Ala Val Glu Trp Glu Ser Asn Gly Gln Pro Glu Asn Asn Tyr Lys
305 310 315 320

Thr Thr Pro Pro Val Leu Asp Ser Asp Gly Ser Phe Phe Leu Tyr Ser
325 330 335

Lys Leu Thr Val Asp Lys Ser Arg Trp Gln Gln Gly Asn Val Phe Ser
340 345 350

Cys Ser Val Met His Glu Ala Leu His Asn His Tyr Thr Gln Lys Ser
355 360 365

Leu Ser Leu
370

<210> SEQ ID NO 101
<211> LENGTH: 453
<212> TYPE: PRT
<213> ORGANISM: Homo sapiens

<400> SEQUENCE: 101

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln

```
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 102
<211> LENGTH: 363
<212> TYPE: DNA
<213> ORGANISM: Artificial Sequence
<220> FEATURE:
<223> OTHER INFORMATION: VH for C1E1

<400> SEQUENCE: 102
gaagtgatgc tggtggagtc tgggggaggg ttagtgaagc ctggagggtc cctgaaactc 60
tcctgtgcag cctctggatt cacgttcagt agttatctta tgtcttgggt tcgccagact 120
ccggagaaga ggctggagtg ggtcgcaacc attagtggtg gtggtggtga cacctacttt 180
ccagacagtg tgaagggtcg attcaccatc tccagagaca atgtcaagaa caacctgtac 240
ctgcaaatga gcagtcttag gtctgaggac acggccttgt attactgtgt aagatttggg 300
ggcgctggtt actactggta tttcgatgtc tggggcgcag ggaccacggt caccgtctcc 360
tca 363

<210> SEQ ID NO 103
<211> LENGTH: 363
<212> TYPE: DNA
<213> ORGANISM: Artificial Sequence
<220> FEATURE:
<223> OTHER INFORMATION: VH for huC1E1-V2 and huC1E1-V10

<400> SEQUENCE: 103
gaggtgcagc tggtggagtc tgggggaggc gtggtccagc ctgggaggtc cctgagactc 60
tcctgtgcag cctctggatt caccttcagt agctatctta tgtcctgggt ccgccaggct 120
ccaggcaagg ggctagagtg ggtggcaact atatcaggtg gtggaggtga cacatacttc 180
ccagactccg tgaagggccg attcaccatc tccagagaca attccaagaa cacgctgtat 240
ctgcaaatga acagcctgag agctgaggac acggctgtgt attactgtgt gagattcggt 300
ggtgctggtt actactggta ctttgacgtc tggggccaag gaaccctggt caccgtctcg 360
agt 363

<210> SEQ ID NO 104
<211> LENGTH: 351
<212> TYPE: DNA
<213> ORGANISM: Artificial Sequence
<220> FEATURE:
<223> OTHER INFORMATION: VH for D1F2

<400> SEQUENCE: 104
gaagtgatgc tggtggagtc tgggggaggc ttagtgaagc ctggagggtc cctgaaactc 60
tcctgtgcag cctctggatt cactttcagt agctatacca tgtcttgggt tcgccagact 120
ccggagaaga ggctggagtg ggtcgcaacc attagtggtg gtggtagtaa catctactat 180
ccagacagtg tggagggtcg attcaccgtc tccagagaca atgccaggaa caccctgtac 240
ctgcatatga gcagtctgag gtctgaggac acggccttat attactgtgt ccttaactac 300
gcctatgcta tggactactg gggtcaagga acctcagtca ccgtctcctc a 351

<210> SEQ ID NO 105
<211> LENGTH: 351
<212> TYPE: DNA
<213> ORGANISM: Artificial Sequence
<220> FEATURE:
<223> OTHER INFORMATION: VH for C1F5

<400> SEQUENCE: 105
gaagtgcagc tggtggagtc tgggggaggc ttagtgaagc ctggagggtc cctgaaactc 60
tcctgtgcag cctctggatt cgctttcagt agctatgaca tgtcttgggt tcgccagact 120
ccggagaaga ggctggagtg ggtcgcatac attactggtg gtggtagtag ttccttctat 180
ccagacactg tgaagggccg attcaccatc tccagagaca attccaagaa caccctgtat 240
ttgcaaatga ccagtctgag gtctgaggac acagccatgt attactgtgc aagcccctac 300
ttatcctact ttgactactg gggccaaggc accactctca cagtctcctc a 351

<210> SEQ ID NO 106
<211> LENGTH: 360
<212> TYPE: DNA
<213> ORGANISM: Artificial Sequence
<220> FEATURE:
<223> OTHER INFORMATION: VH for D1A1

<400> SEQUENCE: 106
gaagtgatgc tggtggagtc tgggggaggc ttagtgaagc ctggagggtc cctgaaactc 60
tcctgtgcag cctctggatt cactttcagt aactatgcca tgtcttgggt tcgccagact 120
ccggagaaga ggctggagtg ggtcgcaacc attagtggtg gtggtggtaa catctactat 180
ccagacagtg tgaagggtcg attcaccatc tccagagaca atgccaggaa caccctgtac 240
ctgcaaatga gcagtctgag gtctgaggac acggccttgt attattgtgc aagcccgtat 300
gctaactacg tatggtacct cgatgtctgg ggcgcaggga ccacggtcac cgtctcctca 360

<210> SEQ ID NO 107
<211> LENGTH: 360
<212> TYPE: DNA
<213> ORGANISM: Artificial Sequence
<220> FEATURE:
<223> OTHER INFORMATION: VH for D1F1

<400> SEQUENCE: 107
gaagtgatgc tggtggagtc tgggggaggc ttagtgaagc ctggagggtc cctgaaactc 60
tcctgtgcag cctctggatt cactttcagt agcaatacca tgtcttgggt tcgccagact 120
ccggagaaga ggctggagtg ggtcgcagcc attagtggtg gtggtgttaa cacctactat 180
ccagacagtg tgaagggtcg attcaccatc tccagagaca atgccaggaa caccctgtac 240
ctgcaaatga gcagtctgag gtctgaggac acggccctgt attactgtgc aagacatggt 300
aactacaatt actatggtat ggactactgg ggtcaaggaa cctcagtcac cgtctcctca 360

<210> SEQ ID NO 108
<211> LENGTH: 360
<212> TYPE: DNA
<213> ORGANISM: Artificial Sequence
<220> FEATURE:
<223> OTHER INFORMATION: VH for C1E2

<400> SEQUENCE: 108
caggtccagt tgcagcagtc tggagctgag ctggtaaggc ctgggacttc agtgaagata 60
tcctgcaagg cttctggcta caccttcact aactactggc taggttgggt aaaacagagg 120
cctggacatg gacttgagtg gattggagat atttaccctg gaggtggtta tactaactac 180
aatgagaact tcaagggcaa ggccacactg actgcagaca catcctccag cactgcctac 240
atgcagctca gtagcctgac atctgaggac tctgctgtct ttttctgtgc aagaggctac 300
ggtactaatt actggtactt cgatgtctgg ggcgcaggga ccacggtcac cgtctcctca 360

-continued

<210> SEQ ID NO 109
<211> LENGTH: 372
<212> TYPE: DNA
<213> ORGANISM: Artificial Sequence
<220> FEATURE:
<223> OTHER INFORMATION: VH for C1A1

<400> SEQUENCE: 109
caagttactc taaaagagtc tggccctggg atattgaagc cctcacagac cctcagtctg 60
acttgttctt tctctgggtt ttcactgagc acttctggta tgggtgtagg ctggattcgt 120
cagccttcag ggaagggtct ggagtggctg gcacacattt ggtgggatga tgataagttc 180
tataacccat ccctgaagag ccagctcaca atctccaagg atacctccag aaaccaggtt 240
ttcctcaaga tcaccagtgt ggacactgca gatactgcca cttactactg tgctcgaacc 300
ggggggttta ttactacggg ctactggtac ttcgatgtct ggggcgcagg gaccacggtc 360
accgtctcct ca 372

<210> SEQ ID NO 110
<211> LENGTH: 354
<212> TYPE: DNA
<213> ORGANISM: Artificial Sequence
<220> FEATURE:
<223> OTHER INFORMATION: VH for C1F4

<400> SEQUENCE: 110
caggtccagc tgcaacagtc tggggctgag ctggtgaggc ctggggtctc agtgaagatt 60
tcctgcaagg gttctggcta caaattcact gattatgcta tgcactgggt gaggcagagt 120
catgcaaaga gtctagagtg gattggaatt attagtactt actctggtga cgttagtttc 180
aaccagaact tcaagggcaa ggccacaatg actgtagaca aatcctccag cacagcctat 240
atggaacttg ccagactgac atctgaggat tctgccatct attactgttc aagactgggg 300
attacggcgg ggtttgctta ctggggccaa gggactctgg tcactgtctc tgca 354

<210> SEQ ID NO 111
<211> LENGTH: 360
<212> TYPE: DNA
<213> ORGANISM: Artificial Sequence
<220> FEATURE:
<223> OTHER INFORMATION: VH for D2C2

<400> SEQUENCE: 111
gaagtgatgc tggtggagtc tgggggaggc ttagtgaagc ctggagggtc cctgaaactc 60
tcctgtgcag cctctggatt cactttcagt agcaatacca tgtcttgggt tcgccagact 120
ccggagaaga ggctggagtg ggtcgcagcc attagtggtg gtggtgttga cacctactat 180
ccagacagtg tgaagggtcg attcaccatc tccagagaca atgccaggaa caccctgtac 240
ctgcaaatga gcagtctgag gtctgaggac acggccctgt attactgtgc aagacatggt 300
aactacaatt actatggtat ggactactgg ggtcaaggaa cctcagtcac cgtctcctca 360

<210> SEQ ID NO 112
<211> LENGTH: 372
<212> TYPE: DNA
<213> ORGANISM: Artificial Sequence
<220> FEATURE:
<223> OTHER INFORMATION: VH for 2G2

<400> SEQUENCE: 112

-continued gaggtgcaac tggtggagtc tgggggagac ttagtgaagc ctggagggtc cctgaaactc 60
tcctgtacag cctctggatt cactttcagt tactatggca tgtcttgggt tcgccagact 120
ccagacaaga ggctggaatg ggtcgcaacc attagtagtg gtagtagttt cacctactct 180
ccagacagtg tgaaggggcg attcaccatc tccagagaca atgccaagaa caccctgtac 240
ctacaaatga acagtctgaa gtctgaggac acagccattt attactgtac aagacgagag 300
gggatctatg atgcttcctg ggattattct atggactact ggggtcaagg aacctcagtc 360
accgtctcct ca 372

<210> SEQ ID NO 113
<211> LENGTH: 363
<212> TYPE: DNA
<213> ORGANISM: Artificial Sequence
<220> FEATURE:
<223> OTHER INFORMATION: VH for C1C5

<400> SEQUENCE: 113
cagatccagt tggtgcagtc aggacctgag ctgaagaagc ctggagagac agtcaagatc 60
tcctgcaagg cttctgggta taccttcaca aactatggaa taaactgggt gaagcaggct 120
ccaggaaagg gtttaaagtg gatgggctgg ataaacacct atagtggaga gccaacatat 180
tctgatgact tcaagggacg ctttgccttc tctttggaaa cctctgccag cactgcctat 240
ttgcagatca acaacctcaa aaatgaggac acgtctacat atttctgtgt aagacagggg 300
gactttgatt acgaggatgc tatggactac tggggtcaag gaacctcagt caccgtctcc 360
tca 363

<210> SEQ ID NO 114
<211> LENGTH: 333
<212> TYPE: DNA
<213> ORGANISM: Artificial Sequence
<220> FEATURE:
<223> OTHER INFORMATION: VL for C1E1

<400> SEQUENCE: 114
gacattgtgc tgacccaatc tccagcttct ttggctgtgt ctctagggca gagggccacc 60
atctcctgca gagccagcaa aagtgttgat gattctggca ttagttttat gcactggttc 120
caacagaaac caggacagcc acccaaactc ctcatctatg ctgcatccaa ccaaggatcc 180
ggggtccctg ccaggtttcg tggcagtggg tctgggacag acttcagcct caacatccat 240
cctatggagg aggatgatac tgcaatgtat ttctgtcacc aaactaagga ggttccgtgg 300
acgttcggtg gaggcaccaa gctggaaatc aaa 333

<210> SEQ ID NO 115
<211> LENGTH: 333
<212> TYPE: DNA
<213> ORGANISM: Artificial Sequence
<220> FEATURE:
<223> OTHER INFORMATION: VL for huC1E1-V7 and huC1E1-V10

<400> SEQUENCE: 115
gaaattgtgt tgacacagtc tccagccacc ctgtctttgt ctccagggga aagagccacc 60
ctctcctgca gggccagtaa gtctgttgac gacagtggta tcagcttcat gcactggtat 120
caacagaaac ctggccaggc tcccaggctc ctcatctatg ctgcatccaa ccagggctct 180
ggcatcccag ccaggttcag tggcagtggg tctgggacag acttcactct caccatcagc 240
agcctagagc ctgaagattt tgcagtttat tactgtcatc agactaagga ggtgccttgg 300
acgttcggcc aagggaccaa ggtggagatc aaa 333

<210> SEQ ID NO 116
<211> LENGTH: 321
<212> TYPE: DNA
<213> ORGANISM: Artificial Sequence
<220> FEATURE:
<223> OTHER INFORMATION: VL for D1F2

<400> SEQUENCE: 116
gatatccaga tgacacagac tacatcctcc ctgtctgcct ctctgggaga cagagtcacc 60
atcagttgca gggccagtca ggacattagc aattttttaa actggtatca gcagaaacca 120
gatggaactg ttaaactcct gatctactac acatcaagat tacagtcagg agtcccatca 180
aggttcagtg gcactgggtc tgggacagat tattctctca ccattagcaa cctggaacaa 240
gaagatcttg ccacttactt ttgccaacag ggtagttcgc ttccgtggac gttcggtgga 300
ggcaccaagc tggaaatcaa a 321

<210> SEQ ID NO 117
<211> LENGTH: 321
<212> TYPE: DNA
<213> ORGANISM: Artificial Sequence
<220> FEATURE:
<223> OTHER INFORMATION: VL for C1F5

<400> SEQUENCE: 117
gatattgtgc taactcagtc tccagccacc ctgtctgtga ctccaggaga tagcgtcagt 60
ctttcctgca gggccagcca aagtattagc aacaacctac actggtatca acaaaaatca 120
catgagtctc caaggcttct catcaagtat ggttcccagt ccatgtctgg gatcccctcc 180
aggttcagtg gcagtggatc agggacagat ttcactctcg ttatcaacag tgtggagact 240
gaagattttg gaatgtattt ctgtcaacag agtaacagct ggcctctcac gttcggtgct 300
gggaccaagc tggagctgaa a 321

<210> SEQ ID NO 118
<211> LENGTH: 321
<212> TYPE: DNA
<213> ORGANISM: Artificial Sequence
<220> FEATURE:
<223> OTHER INFORMATION: VL for D1A1

<400> SEQUENCE: 118
gatatccaga tgacacagac tacatcctcc ctgtctgcct ctctgggaga cagagtcacc 60
atcagttgca gggcaagtca ggacattagc aattatttaa actggtatca gcagaaacca 120
gatggaactg ttaaactcct gatctactac acatcaagat tacactcagg agtcccatca 180
aggttcagtg gcagtgggtc tggaacagat ttttctctca ccattagcaa cctggaagaa 240
gaagatattg ccacttactt ttgccaacag agtaatgcgc ttccgtggac gttcggtgga 300
ggcaccaaac tggaaatcaa a 321

<210> SEQ ID NO 119
<211> LENGTH: 333
<212> TYPE: DNA
<213> ORGANISM: Artificial Sequence
<220> FEATURE:
<223> OTHER INFORMATION: VL for D1F1

<400> SEQUENCE: 119

```
gacattgtgc tgacccaatc tccagcttct ttggttgtgt ctctagggca gagggccacc     60

atctcctgca gagccagcga aagtgttgat aattctggca ttagttttat gaactggttc    120

caacagaaac caggacagcc acccaaactc ctcatctata ctgcatccaa ccaaggatcc    180

ggggtccctg ccaggtttag tggcagtggg tctgggacag acttcagcct caacatccat    240

cctatggagg aggatgattc tgcaatgtat ttctgtcagc aaagttatga ggttccttgg    300

acgttcggtg gaggcaccaa gctggaaatc aaa                                 333


<210> SEQ ID NO 120
<211> LENGTH: 321
<212> TYPE: DNA
<213> ORGANISM: Artificial Sequence
<220> FEATURE:
<223> OTHER INFORMATION: VL for C1E2

<400> SEQUENCE: 120

agtattgtga tgacccagac tcccaaattc ctgcttgtat cagcaggaga cagggttacc     60

ataacctgca aggccagtca gagtgtgagt aatgatgtag cttggtacca acagaagcca    120

gggcagtctc ctaaactgct gatatactat gcatttcatc gctacactgg agtccctgat    180

cgcttcactg gcagtggata tgggacggat ttcactttca ccatcagcac tgtgcaggct    240

gaagacctgg cagtttattt ctgtcagcag gattatagct ctccgtacac gttcggaggg    300

gggaccaagc tggaaataaa a                                              321


<210> SEQ ID NO 121
<211> LENGTH: 321
<212> TYPE: DNA
<213> ORGANISM: Artificial Sequence
<220> FEATURE:
<223> OTHER INFORMATION: VL for C1A1

<400> SEQUENCE: 121

gatatccaga tgacacagac tacatcctcc ctgtctgcct ctctgggaga cagagtcacc     60

atcagttgca gggcaagtca ggacattagc aattatttaa tctggtatca gcagaaaaca    120

gatggaactc ttaaactcct gatctactac acatcaagat tacactcagg agtcccatca    180

aggttcagtg gcagtgggtc tggaacagat tattctctca ccattagcaa cctggagcaa    240

gaagatattg ccacttactt ttgccagcag cataaaacgc ttccgtggac gttcggtgga    300

ggcaccaagc tggaaatcaa a                                              321


<210> SEQ ID NO 122
<211> LENGTH: 321
<212> TYPE: DNA
<213> ORGANISM: Artificial Sequence
<220> FEATURE:
<223> OTHER INFORMATION: VL for C1F4

<400> SEQUENCE: 122

gacattgtga tgacccagtc tcaaaaattc atgtccacat cagtaggaga cagggtcacc     60

atcacctgca aggccagtca gaatgttcgt actgctgtag cctggtatca acagaaacca    120

gggcagtctc ctaaagcact gatttacttg gcatccaacc ggcacactgg agtccctgat    180

cgcttcacag gcagtggatc tgggacagat ttcactctca ccattagcaa tgtgcaatct    240

aaagacctgg cagattattt ctgtctgcaa cattggaatt atccgtacac gttcggaggg    300

gggaccaagc tggaaataaa a                                              321
```

<210> SEQ ID NO 123
<211> LENGTH: 333
<212> TYPE: DNA
<213> ORGANISM: Artificial Sequence
<220> FEATURE:
<223> OTHER INFORMATION: VL for D2C2

<400> SEQUENCE: 123
gacattgtgc tgacccaatc tccagcttct ttggctgtgt ctctagggca gagggccacc 60
atctcctgca gagccagcga aagtgttgat aattctggca ttagttttat gaactggttc 120
caacagaaac caggacagtc acccaaactc ctcatctata ttgcatccaa ccacggatcc 180
ggggtccctg ccaggtttag tggcagtggg tctgggacag acttcagcct caacatccat 240
cctatggagg aggatgattc tgcaatgtat ttctgtcagc aaagttatga ggttccttgg 300
acgttcggtg gaggcaccaa gctggaaatc aaa 333

<210> SEQ ID NO 124
<211> LENGTH: 336
<212> TYPE: DNA
<213> ORGANISM: Artificial Sequence
<220> FEATURE:
<223> OTHER INFORMATION: VL for 2G2

<400> SEQUENCE: 124
gatgttttga tgacccaaac tccactctcc ctgcctgtca gtcttggaga tcaagcctcc 60
atctcttgca gatctagtca gagcattata cgtagtaatg gaaacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgacga tctgggactt tattactgct ttcaaggttc acatgttccg 300
tggacgttcg gtggaggcac caagctggaa atcaaa 336

<210> SEQ ID NO 125
<211> LENGTH: 330
<212> TYPE: DNA
<213> ORGANISM: Artificial Sequence
<220> FEATURE:
<223> OTHER INFORMATION: VL for C1C5

<400> SEQUENCE: 125
gatgttttga tgacccaaag tccactctcc ctgcctgtca gtcttggaga tcaagcctcc 60
atctcttgca gatctagtca gagtattgta catagtaatg gacacatcta tttagaatgg 120
tacctgcaga aaccaggcca gtctccaaag ctcctgatct acaaagtttc caagcgattt 180
tctggggtcc cagacaggtt cagtggcagt ggatcaggga cagatttcac actcaagatc 240
agcagagtgg aggctgagga tctgggagtt tattactgct ttcaaggttc acatgggacg 300
ttcggtggag gcaccaagct ggaaatcaaa 330

<210> SEQ ID NO 126
<211> LENGTH: 990
<212> TYPE: DNA
<213> ORGANISM: Artificial Sequence
<220> FEATURE:
<223> OTHER INFORMATION: human IgG1 heavy chain constant region

<400> SEQUENCE: 126
gctagcacca agggcccatc ggtcttcccc ctggcaccct cctccaagag cacctctggg 60
ggcacagcgg ccctgggctg cctggtcaag gactacttcc ccgaaccggt gacggtgtcg 120

```
tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990


<210> SEQ ID NO 127
<211> LENGTH: 321
<212> TYPE: DNA
<213> ORGANISM: Artificial Sequence
<220> FEATURE:
<223> OTHER INFORMATION: human kappa light chain constant region

<400> SEQUENCE: 127

cgtacggtgg cggcgccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg t                                              321


<210> SEQ ID NO 128
<211> LENGTH: 294
<212> TYPE: DNA
<213> ORGANISM: Artificial Sequence
<220> FEATURE:
<223> OTHER INFORMATION: human IgG1 heavy chain CH1 region

<400> SEQUENCE: 128

gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agtt          294


<210> SEQ ID NO 129
<211> LENGTH: 324
<212> TYPE: PRT
<213> ORGANISM: Artificial Sequence
<220> FEATURE:
<223> OTHER INFORMATION: Heavy chain constant region for mouse
```

antibodies

<400> SEQUENCE: 129

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

<210> SEQ ID NO 130
<211> LENGTH: 107
<212> TYPE: PRT
<213> ORGANISM: Artificial Sequence
<220> FEATURE:
<223> OTHER INFORMATION: Light chain constant region for mouse antibodies

<400> SEQUENCE: 130

```
Arg Ala Asp Ala Ala Pro Thr Val Ser Ile Phe Pro Pro Ser Ser Glu
1               5                   10                  15
```

-continued

```
Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Gly Glu Cys
            100                 105
```